(12) United States Patent
Rourke et al.

(10) Patent No.: US 9,011,531 B2
(45) Date of Patent: Apr. 21, 2015

(54) METHOD AND APPARATUS FOR REPAIRING A MITRAL VALVE

(71) Applicant: MitraSpan, Inc., Belmont, MA (US)

(72) Inventors: Jonathan M. Rourke, Belmont, MA (US); Stanley B. Kyi, Andover, MA (US)

(73) Assignee: MitraSpan, Inc., Belmont, MA (US)

( * ) Notice: Subject to any disclaimer, the term of this patent is extended or adjusted under 35 U.S.C. 154(b) by 0 days.

(21) Appl. No.: 13/766,521

(22) Filed: Feb. 13, 2013

(65) Prior Publication Data

US 2013/0211513 A1     Aug. 15, 2013

Related U.S. Application Data

(60) Provisional application No. 61/598,047, filed on Feb. 13, 2012, provisional application No. 61/740,901, filed on Dec. 21, 2012.

(51) Int. Cl.
A61F 2/24       (2006.01)
A61B 17/04      (2006.01)
(Continued)

(52) U.S. Cl.
CPC ............ *A61F 2/2442* (2013.01); *A61F 2/2466* (2013.01); *A61B 2017/22044* (2013.01); *A61B 17/0401* (2013.01); *A61B 17/0485* (2013.01); *A61B 2017/00243* (2013.01);
(Continued)

(58) Field of Classification Search
CPC ....................................................... A61F 2/24
USPC .................... 623/2.37; 606/139, 144, 232
See application file for complete search history.

(56) References Cited

U.S. PATENT DOCUMENTS 5,450,860 A    9/1995   O'Connor
5,593,424 A    1/1997   Northrup
(Continued)

FOREIGN PATENT DOCUMENTS

WO    WO 2004/082523    9/2004
WO    WO 2005/097002    10/2005
(Continued)

OTHER PUBLICATIONS

Tomasz A. Timek et al., Septal-lateral Annular Cinching Abolishes Acute Ischemic Mitral Regurgitation, The Journal of Thoracic and Cardiovascular Surgery, May 2002, vol. 123, No. 5, pp. 881-888.
(Continued)

*Primary Examiner* — Thomas J Sweet
*Assistant Examiner* — Matthew Schall
(74) *Attorney, Agent, or Firm* — Pandiscio & Pandiscio

(57) ABSTRACT

A method for repairing a mitral valve, the method comprising:
positioning a crossing guidewire across the mitral valve, the crossing guidewire passing through the annulus of the mitral valve at a first location and passing through the annulus of the mitral valve at a second location;
using the crossing guidewire to position a spanning implant across the mitral valve, with the spanning implant extending from the first location to the second location;
anchoring the spanning implant at the first location;
tensioning the spanning implant so as to draw the first location and the second location together; and
anchoring the spanning implant at the second location.

19 Claims, 16 Drawing Sheets

(51) Int. Cl.
  *A61B 17/22* (2006.01)
  *A61B 17/00* (2006.01)
  *A61B 17/06* (2006.01)

(52) U.S. Cl.
  CPC .............. *A61B 2017/00477* (2013.01); *A61B 2017/00557* (2013.01); *A61B 2017/00783* (2013.01); *A61B 2017/0409* (2013.01); *A61B 2017/0417* (2013.01); *A61B 2017/0464* (2013.01); *A61B 2017/06104* (2013.01); *A61B 2017/22038* (2013.01)

(56) References Cited

U.S. PATENT DOCUMENTS

| | | | |
|---|---|---|---|
| 5,709,695 A | 1/1998 | Northrup, III | |
| 5,860,992 A | 1/1999 | Daniel et al. | |
| 5,961,440 A | 10/1999 | Schweich et al. | |
| 5,961,539 A | 10/1999 | Northrup, III et al. | |
| 5,972,030 A | 10/1999 | Garrison et al. | |
| 6,210,432 B1 | 4/2001 | Solem et al. | |
| 6,406,420 B1 | 6/2002 | McCarthy et al. | |
| 6,514,194 B2 | 2/2003 | Schweich, Jr. et al. | |
| 6,537,198 B1 | 3/2003 | Vidlund et al. | |
| 6,562,052 B2 | 5/2003 | Nobles et al. | |
| 6,676,702 B2 | 1/2004 | Mathis | |
| 6,695,866 B1 | 2/2004 | Kuehn et al. | |
| 6,752,813 B2 | 6/2004 | Goldfarb et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,893,459 B1 | 5/2005 | Macoviak | |
| 6,908,478 B2 | 6/2005 | Alferness et al. | |
| 6,949,122 B2 | 9/2005 | Adams et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,989,028 B2 | 1/2006 | Lashinski et al. | |
| 7,004,958 B2 | 2/2006 | Adams et al. | |
| 7,011,682 B2 | 3/2006 | Lashinski et al. | |
| 7,037,334 B1 | 5/2006 | Hlavka et al. | |
| 7,044,967 B1 | 5/2006 | Solem et al. | |
| 7,083,628 B2 | 8/2006 | Bachman | |
| 7,087,064 B1 | 8/2006 | Hyde | |
| 7,090,695 B2 | 8/2006 | Solem et al. | |
| 7,112,207 B2 | 9/2006 | Allen et al. | |
| 7,112,219 B2 | 9/2006 | Vidlund et al. | |
| 7,125,421 B2 | 10/2006 | Tremulis et al. | |
| 7,179,282 B2 | 2/2007 | Alferness et al. | |
| 7,189,201 B2 | 3/2007 | Borst et al. | |
| 7,270,676 B2 | 9/2007 | Alferness et al. | |
| 7,296,577 B2 | 11/2007 | Lashinski et al. | |
| 7,300,462 B2 | 11/2007 | Swinford et al. | |
| 7,311,728 B2 | 12/2007 | Solem et al. | |
| 7,351,259 B2 | 4/2008 | Swinford et al. | |
| 7,364,588 B2 | 4/2008 | Mathis et al. | |
| 7,381,210 B2 | 6/2008 | Zarbatany et al. | |
| 7,431,726 B2 | 10/2008 | Spence et al. | |
| 7,503,932 B2 | 3/2009 | Mathis et al. | |
| 7,563,273 B2 | 7/2009 | Goldfarb et al. | |
| 7,588,582 B2 | 9/2009 | Starksen et al. | |
| 7,591,826 B2 | 9/2009 | Alferness et al. | |
| 7,608,091 B2 | 10/2009 | Goldfarb et al. | |
| 7,608,102 B2 | 10/2009 | Adams et al. | |
| 7,618,449 B2 | 11/2009 | Tremulis et al. | |
| 7,635,386 B1 | 12/2009 | Gammie | |
| 7,637,946 B2 | 12/2009 | Solem et al. | |
| 7,655,015 B2 | 2/2010 | Goldfarb et al. | |
| 7,655,040 B2 | 2/2010 | Douk et al. | |
| 7,665,040 B2 | 2/2010 | Nakamura | |
| 7,666,193 B2 | 2/2010 | Starksen et al. | |
| 7,666,224 B2 | 2/2010 | Vidlund et al. | |
| 7,682,369 B2 | 3/2010 | Séguin | |
| 7,736,388 B2 | 6/2010 | Goldfarb et al. | |
| 7,740,638 B2 | 6/2010 | Hyde | |
| 7,753,923 B2 | 7/2010 | St. Goar et al. | |
| 7,758,595 B2 | 7/2010 | Allen et al. | |
| 7,758,637 B2 | 7/2010 | Starksen et al. | |
| 7,799,073 B2 | 9/2010 | Khalapyan | |
| 7,803,167 B2 | 9/2010 | Nobles et al. | |
| 7,811,296 B2 | 10/2010 | Goldfarb et al. | |
| 7,846,179 B2 | 12/2010 | Belef et al. | |
| 7,860,555 B2 | 12/2010 | Saadat | |
| 7,871,368 B2 | 1/2011 | Zollinger et al. | |
| 7,871,433 B2 | 1/2011 | Lattouf | |
| 7,887,552 B2 | 2/2011 | Bachman | |
| 7,905,892 B2 | 3/2011 | Nobles et al. | |
| 7,935,145 B2 | 5/2011 | Alfieri et al. | |
| 7,935,146 B2 | 5/2011 | Langberg et al. | |
| 7,967,833 B2 | 6/2011 | Sterman et al. | |
| 7,998,151 B2 | 8/2011 | St. Goar et al. | |
| 8,029,518 B2 | 10/2011 | Goldfarb et al. | |
| 8,029,565 B2 | 10/2011 | Lattouf | |
| 8,043,368 B2 | 10/2011 | Crabtree | |
| 8,052,592 B2 | 11/2011 | Goldfarb et al. | |
| 8,066,766 B2 | 11/2011 | To et al. | |
| 8,070,805 B2 | 12/2011 | Vidlund et al. | |
| 8,127,323 B2 | 2/2012 | Ando et al. | |
| 8,133,272 B2 | 3/2012 | Hyde | |
| 8,142,493 B2 | 3/2012 | Spence et al. | |
| 8,163,010 B1 | 4/2012 | Hausen | |
| 8,187,207 B2 | 5/2012 | Machold et al. | |
| 8,187,299 B2 | 5/2012 | Goldfarb et al. | |
| 8,262,725 B2 | 9/2012 | Subramanian | |
| 8,382,829 B1 | 2/2013 | Call et al. | |
| 8,454,656 B2 | 6/2013 | Tuval | |
| 8,470,028 B2 | 6/2013 | Thornton et al. | |
| 2002/0013571 A1 | 1/2002 | Goldfarb et al. | |
| 2002/0087173 A1 | 7/2002 | Alferness et al. | |
| 2003/0069636 A1 | 4/2003 | Solem et al. | |
| 2003/0083538 A1 | 5/2003 | Adams et al. | |
| 2003/0105520 A1 | 6/2003 | Alferness et al. | |
| 2003/0120264 A1 | 6/2003 | Lattouf | |
| 2003/0120340 A1 | 6/2003 | Liska et al. | |
| 2003/0130731 A1 | 7/2003 | Vidlund et al. | |
| 2003/0144697 A1 | 7/2003 | Mathis et al. | |
| 2003/0171776 A1 | 9/2003 | Adams et al. | |
| 2003/0171806 A1 | 9/2003 | Mathis et al. | |
| 2003/0191497 A1 | 10/2003 | Cope | |
| 2004/0039443 A1 | 2/2004 | Solem et al. | |
| 2004/0102840 A1 | 5/2004 | Solem et al. | |
| 2004/0127983 A1 | 7/2004 | Mortier et al. | |
| 2004/0153147 A1 | 8/2004 | Mathis | |
| 2004/0158321 A1 | 8/2004 | Reuter et al. | |
| 2004/0181238 A1 | 9/2004 | Zarbatany et al. | |
| 2004/0225300 A1 | 11/2004 | Goldfarb et al. | |
| 2004/0243227 A1 | 12/2004 | Starksen et al. | |
| 2005/0004667 A1 | 1/2005 | Swinford et al. | |
| 2005/0027351 A1 | 2/2005 | Reuter et al. | |
| 2005/0038507 A1 | 2/2005 | Alferness et al. | |
| 2005/0075723 A1 | 4/2005 | Schroeder et al. | |
| 2005/0080483 A1 | 4/2005 | Solem et al. | |
| 2005/0137685 A1 | 6/2005 | Nieminen et al. | |
| 2005/0149182 A1 | 7/2005 | Alferness et al. | |
| 2005/0209690 A1 | 9/2005 | Mathis et al. | |
| 2005/0216078 A1 | 9/2005 | Starksen et al. | |
| 2005/0222678 A1 | 10/2005 | Lashinski et al. | |
| 2005/0261704 A1 | 11/2005 | Mathis | |
| 2006/0004443 A1 | 1/2006 | Liddicoat et al. | |
| 2006/0020335 A1 | 1/2006 | Kowalsky et al. | |
| 2006/0020336 A1* | 1/2006 | Liddicoat .................... 623/2.37 |
| 2006/0025750 A1 | 2/2006 | Starksen et al. | |
| 2006/0025784 A1 | 2/2006 | Starksen et al. | |
| 2006/0030885 A1 | 2/2006 | Hyde | |
| 2006/0058817 A1 | 3/2006 | Starksen et al. | |
| 2006/0116757 A1 | 6/2006 | Lashinski et al. | |
| 2006/0116758 A1 | 6/2006 | Swinford et al. | |
| 2006/0241340 A1 | 10/2006 | Schroeder et al. | |
| 2006/0271174 A1 | 11/2006 | Nieminen et al. | |
| 2006/0276890 A1 | 12/2006 | Solem et al. | |
| 2007/0038293 A1 | 2/2007 | St. Goar et al. | |
| 2007/0038297 A1 | 2/2007 | Bobo, Jr. et al. | |
| 2007/0061010 A1 | 3/2007 | Hauser et al. | |
| 2007/0066879 A1 | 3/2007 | Mathis et al. | |

(56) References Cited

U.S. PATENT DOCUMENTS

| | | |
|---|---|---|
| 2007/0073391 A1 | 3/2007 | Bourang et al. |
| 2007/0080188 A1 | 4/2007 | Spence et al. |
| 2007/0093857 A1 | 4/2007 | Rogers et al. |
| 2007/0112424 A1 | 5/2007 | Spence et al. |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0135912 A1 | 6/2007 | Mathis |
| 2007/0173926 A1 | 7/2007 | Bobo, Jr. et al. |
| 2007/0185572 A1 | 8/2007 | Solem et al. |
| 2007/0276414 A1 | 11/2007 | Nobles |
| 2007/0276437 A1 | 11/2007 | Call et al. |
| 2008/0058839 A1 | 3/2008 | Nobles et al. |
| 2008/0140191 A1 | 6/2008 | Mathis et al. |
| 2008/0167714 A1 | 7/2008 | St. Goar et al. |
| 2008/0183194 A1 | 7/2008 | Goldfarb et al. |
| 2008/0228165 A1 | 9/2008 | Spence et al. |
| 2008/0228266 A1 | 9/2008 | McNamara et al. |
| 2008/0228267 A1 | 9/2008 | Spence et al. |
| 2008/0234704 A1 | 9/2008 | Starksen et al. |
| 2008/0243150 A1 | 10/2008 | Starksen et al. |
| 2008/0243245 A1 | 10/2008 | Thambar et al. |
| 2008/0262609 A1 | 10/2008 | Gross et al. |
| 2008/0269786 A1 | 10/2008 | Nobles et al. |
| 2008/0275503 A1 | 11/2008 | Spence et al. |
| 2009/0082619 A1 | 3/2009 | De Marchena |
| 2009/0137863 A1 | 5/2009 | Schweich, Jr. et al. |
| 2009/0259307 A1 | 10/2009 | Gross et al. |
| 2010/0016958 A1 | 1/2010 | St. Goar et al. |
| 2010/0022823 A1 | 1/2010 | Goldfarb et al. |
| 2010/0023118 A1 | 1/2010 | Medlock et al. |
| 2010/0030242 A1 | 2/2010 | Nobles et al. |
| 2010/0030330 A1 | 2/2010 | Bobo et al. |
| 2010/0042147 A1 | 2/2010 | Janovsky et al. |
| 2010/0070028 A1 | 3/2010 | Sugimoto |
| 2010/0094317 A1 | 4/2010 | Goldfarb et al. |
| 2010/0100108 A1 | 4/2010 | Goldfarb et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0174297 A1 | 7/2010 | Speziali |
| 2010/0185278 A1 | 7/2010 | Schankereli |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2010/0318184 A1 | 12/2010 | Spence |
| 2010/0324669 A1 | 12/2010 | Hlavka et al. |
| 2011/0004227 A1 | 1/2011 | Goldfarb et al. |
| 2011/0009957 A1 | 1/2011 | Langberg et al. |
| 2011/0015655 A1 | 1/2011 | Nobles et al. |
| 2011/0015722 A1 | 1/2011 | Hauser et al. |
| 2011/0022166 A1 | 1/2011 | Dahlgren et al. |
| 2011/0082538 A1 | 4/2011 | Dahlgren et al. |
| 2011/0106245 A1 | 5/2011 | Miller et al. |
| 2011/0106247 A1 | 5/2011 | Miller et al. |
| 2011/0112632 A1 | 5/2011 | Chau et al. |
| 2011/0125189 A1 | 5/2011 | Stoll, Jr. et al. |
| 2011/0137397 A1 | 6/2011 | Chau et al. |
| 2011/0190793 A1 | 8/2011 | Nobles et al. |
| 2011/0238165 A1 | 9/2011 | Seguin |
| 2011/0257728 A1 | 10/2011 | Kuehn |
| 2011/0270276 A1 | 11/2011 | Rothstein et al. |
| 2011/0288637 A1 | 11/2011 | De Marchena |
| 2011/0313434 A1 | 12/2011 | Kocaturk |
| 2012/0029628 A1 | 2/2012 | Rowe |
| 2012/0078358 A1 | 3/2012 | Vidlund et al. |
| 2012/0083806 A1 | 4/2012 | Goertzen |
| 2012/0095552 A1 | 4/2012 | Spence et al. |
| 2012/0109155 A1 | 5/2012 | Robinson et al. |
| 2012/0123531 A1 | 5/2012 | Tsukashima et al. |
| 2012/0130405 A1 | 5/2012 | Cohn et al. |
| 2012/0143323 A1 | 6/2012 | Hasenkam et al. |
| 2012/0209376 A1 | 8/2012 | Hauser et al. |
| 2013/0103055 A1 | 4/2013 | Schaller et al. |
| 2013/0103140 A1 | 4/2013 | Subramanian et al. |
| 2013/0110230 A1 | 5/2013 | Solem |
| 2013/0116780 A1 | 5/2013 | Miller et al. |
| 2013/0190863 A1 | 7/2013 | Call et al. |
| 2013/0282059 A1 | 10/2013 | Ketai et al. |
| 2013/0338764 A1 | 12/2013 | Thornton et al. |
| 2014/0100420 A1 | 4/2014 | Mortier et al. |
| 2014/0148825 A1 | 5/2014 | Nobles et al. |
| 2014/0222138 A1 | 8/2014 | Machold et al. |

FOREIGN PATENT DOCUMENTS

| | | |
|---|---|---|
| WO | WO 2010/093837 | 8/2010 |
| WO | WO 2011/047168 | 4/2011 |
| WO | WO 2011/047201 | 4/2011 |
| WO | WO 2012/036798 | 3/2012 |

OTHER PUBLICATIONS

Frederick A. Tibavan et al., Does Septal-lateral Annular Cinching Work for Chronic Ischemic Mitral Regurgitation?, The Journal of Thoracic and Cardiovascular Surgery, Mar. 2004, vol. 127, No. 3. pp. 654-663.

* cited by examiner

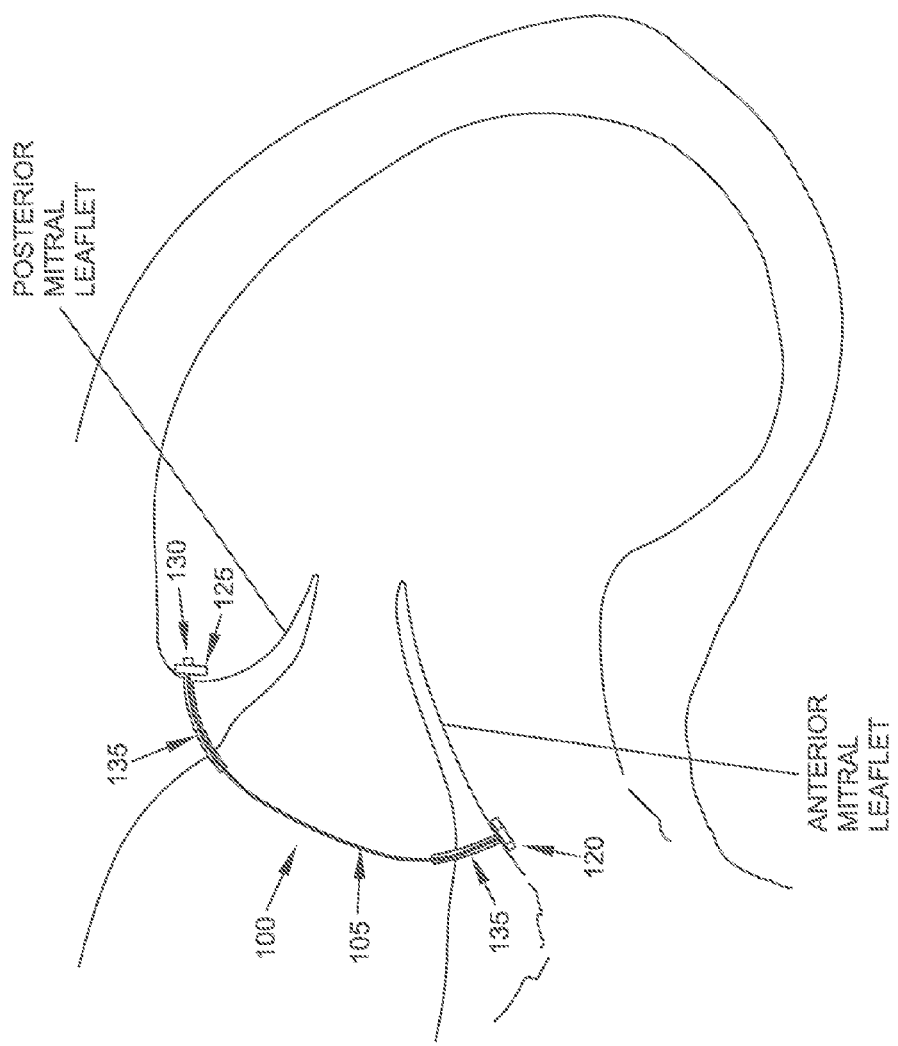

METHOD AND APPARATUS FOR REPAIRING A MITRAL VALVE

REFERENCE TO PENDING PRIOR PATENT APPLICATIONS

This patent application claims benefit of:

(i) prior U.S. Provisional Patent Application Ser. No. 61/598,047, filed Feb. 13, 2012 by Jonathan M. Rourke et al. for METHODS AND DEVICES FOR MITRAL VALVE REPAIR; and (ii) prior U.S. Provisional Patent Application Ser. No. 61/740,901, filed Dec. 21, 2012 by Jonathan M. Rourke et al. for METHODS AND DEVICES FOR MITRAL VALVE REPAIR.

The two (2) above-identified patent applications are hereby incorporated herein by reference.

FIELD OF THE INVENTION

This invention relates to methods and apparatus for performing cardiac structural repairs in general and, more particularly, to methods and apparatus for performing mitral valve repairs and beneficial left ventricular structural repairs.

BACKGROUND OF THE INVENTION

The mitral valve is located in the heart between the left atrium and the left ventricle. A properly functioning mitral valve permits blood to flow from the left atrium to the left ventricle when the left ventricle expands (i.e., during diastole), and prevents the regurgitation of blood from the left ventricle back into the left atrium when the left ventricle contracts (i.e., during systole).

In some circumstances the mitral valve may fail to function properly, such that regurgitation may occur. By way of example but not limitation, mitral regurgitation is a common occurrence in patients with heart failure. Mitral regurgitation in patients with heart failure is caused by changes in the geometric configurations of the left ventricle, papillary muscles and mitral annulus. These geometric alterations result in incomplete coaptation of the mitral leaflets at systole. In this situation, mitral regurgitation is generally corrected by plicating the mitral valve annulus so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to draw the annulus, in a purse-string-like fashion, to a smaller radius, thereby improving leaflet coaptation and reducing mitral regurgitation.

This method of mitral valve repair, generally referred to as "annuloplasty", effectively reduces mitral regurgitation in heart failure patients. This, in turn, reduces symptoms of heart failure, improves quality of life and increases longevity. Unfortunately, however, the invasive nature of such mitral valve surgery (i.e., general anesthesia, chest wall incision, cardiopulmonary bypass, cardiac and pulmonary arrest, an incision on the heart itself so as to gain access to the mitral valve, etc.), and the risks associated therewith, render most heart failure patients poor surgical candidates for an annuloplasty. Thus, a less invasive means to increase leaflet coaptation and thereby reduce mitral regurgitation in heart failure patients would make mitral repair available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for other medical, interventional or surgical therapy.

SUMMARY OF THE INVENTION

As a result, one object of the present invention is to provide an improved method for reducing mitral regurgitation.

Another object of the present invention is to provide improved apparatus for reducing mitral regurgitation.

Another object of the present invention is to provide a method and apparatus for cardiac valve repair, and particularly mitral valve repair, that avoid certain disadvantages of the prior art.

Another object of the present invention is to enable mitral valve repair in a minimally invasive manner without the need for cardiopulmonary bypass or significant surgical intervention.

Another object of the present invention is to provide a means for placing one or more spanning sutures across the mitral valve, and anchoring those spanning sutures to the mitral annulus and nearby cardiac structures, in such a manner as to effect a beneficial reduction in the dilation and distortion of the mitral annulus which causes mitral regurgitation.

The method and apparatus have a further object to provide a means to favorably remodel the left ventricle.

Another object of the present invention is to provide a method and apparatus for mitral valve repair, either via transapical access with a small exposure incision to the skin in the vicinity of the apex of the left ventricle, complete percutaneous access to the left ventricle, or a combination of transapical and percutaneous access including trans-septal puncture or retrograde access through the aorta and aortic valve. In any case, it is an object to provide procedure access through the left ventricular wall to the interior of the left ventricle via a small diameter apical access sheath or access/closure device.

A related object of the present invention is to provide a method and apparatus that do not require a sternotomy when providing procedure access to the mitral valve.

Another related object of the present invention is to provide a method and apparatus that do not require cardiopulmonary bypass or aortic manipulation when reducing mitral regurgitation.

Another object of the present invention is to provide a method and apparatus for mitral valve repair that provides for a controllable anterior/posterior dimension change while a functional improvement in valve competence is continuously evaluated by real-time cardiac ultrasound or other diagnostic means.

One preferred embodiment of the present invention comprises the provision and use of novel, low-profile devices that are sequentially inserted into the left ventricle of the heart, deploy a spanning suture across the mitral valve on the atrial side, anchor the spanning suture to one side of the annulus with a first anchor, adjust the length of the spanning suture crossing the left atrium while performing real-time ultrasound evaluation of mitral regurgitation, and permanently terminate the spanning suture to a second anchor on the other side of the annulus. The present invention provides novel tools that allow this novel process to be performed quickly, easily and safely, by one of several possible approaches, optionally multiple times on a given valve, until satisfactory correction of the mitral regurgitation has been achieved.

A well-known limitation of prior art devices is that they are not broadly effective because of the high degree of variation in patient anatomies. Significantly, the present invention provides a method and apparatus that will provide a high degree of effectiveness across a wide range of patient anatomies, particularly in allowing a clinician to adjust their technique based upon observation of the effectiveness of the initial adjustment of the spanning suture and to increase or decrease the magnitude of the adjustment made on the valve until an acceptable correction has been achieved.

In one preferred embodiment of the present invention, the procedure is generally as follows. External access is established to the left ventricular apex using conventional transapical techniques (e.g., such as those used in the positioning of aortic valves). The left ventricular apex is exposed, either surgically through incision or via direct needle access using the Seldinger technique. An apical access sheath having an internal working diameter of approximately 3-5 mm is passed through the myocardium and directed towards the center of the mitral valve. A first positioning sheath is passed into the left ventricle via the apical access sheath and the distal tip of the first positioning sheath is positioned against the annulus of the valve at a structurally advantageous point. Once proper positioning is verified (e.g., by imaging, either via echocardiography or fluoroscopy), a first curved tube is advanced out of the first positioning sheath and through the annulus. A first guidewire is passed through the first curved tube (and hence through the annulus) and into the left atrium. The first guidewire preferably has an atraumatic tip to avoid damaging the atrial wall and/or surrounding tissues and is visible via ultrasonic or fluoroscopic imaging.

Separately, a center sheath is advanced through the apical access sheath and through the leaflets of the mitral valve so that the distal end of the center sheath is positioned in the left atrium. This center sheath may be placed before or after the aforementioned puncture crossing of the mitral annulus via the first positioning sheath, first curved tube and first guidewire. A snare is then advanced through the center sheath. Under ultrasonic and/or fluoroscopic guidance, the first guidewire and snare are manipulated so that the first guidewire is captured by the snare, and then the snare is used to bring the first guidewire out to the operative sterile field through the center sheath. The first positioning sheath and its associated annulus-crossing first curved tube are then withdrawn, leaving the first guidewire extending from the apex, across the left ventricle, through one side of the annulus, into the left atrium, into the center sheath, between the mitral leaflets and then back across the left ventricle.

The annulus puncture process is then repeated on the opposite side of the annulus, e.g., using a second positioning sheath and an associated annulus-crossing second curved tube. Once the second curved tube has been placed across the annulus, a second guidewire is passed through the annulus-crossing second curved tube and advanced into the left atrium. Then a snare is advanced through the center sheath and captures the distal end of the second guidewire. At this point the snare is retracted so as to bring the second guidewire out to the operative sterile field through the center sheath. Once the distal ends of the first and second guidewires have been brought out to the operative sterile field, they are terminated (i.e., connected) together, and the termination is sent back up through the center sheath so that the termination resides in the left atrium.

Once the first and second guidewires have been passed through opposing sides of the annulus, terminated (i.e., joined) to one another, and their termination advanced back to the left atrium, the termination between the two guidewires is pulled through the second positioning sheath and its annulus-crossing second curved tube, thereby establishing a continuous loop of guidewire extending from the apex, across the left ventricle, through one side of the annulus, across the left atrium, through the other side of the annulus, across the left ventricle, and back down to the apex.

The aforementioned continuous section of guidewire is sometimes hereinafter referred to as "the crossing guidewire".

And the aforementioned approach for placing the crossing guidewire is sometimes hereinafter referred to as the "cross and snare" approach.

It should be appreciated that the term "crossing guidewire" is intended to be a broad term of art, since in fact the construction of the crossing "guidewire" may be effected with wire, suture, filaments, coils, and/or other materials known in the art capable of establishing a spanning structure able to provide the desired device handling in vivo.

In an alternative embodiment of the present invention, the crossing guidewire can be established using a somewhat different approach, which will sometimes hereinafter be referred to as the "cross and catch" approach. More particularly, with the "cross and catch" approach, a first positioning sheath is passed into the left ventricle via the apical access sheath and its distal end is positioned against the annulus at a first location. Then a first curved tube is advanced out of the first positioning sheath and through the annulus at that first location. Next, a second positioning sheath is passed into the left ventricle via the apical access sheath and its distal end is positioned against the annulus at a second location. Then a second curved tube is advanced out of the second positioning sheath and through the annulus at that second location.

Next, a funnel-shaped snare is advanced through the second curved tube of the second positioning sheath so that the funnel-shaped snare faces the first curved tube exiting the first positioning sheath. Then a guidewire is advanced through the first curved tube of the first positioning sheath, across the left atrium and into the funnel-shaped snare exiting the second curved tube of the second positioning sheath. The funnel-shaped snare captures the distal end of the guidewire, and then the funnel-shaped snare is retracted through the second curved tube of the second positioning sheath until the distal end of the guidewire emerges at the operative sterile field. The first positioning sheath and its associated annulus-crossing first curved tube are withdrawn, and the second positioning sheath and its associated annulus-crossing second curved tube are withdrawn, leaving the guidewire extending from the apex, across the left ventricle, through one side of the annulus, into the left atrium, through the other side of the annulus, across the left ventricle and back down to the apex.

In another alternative embodiment of the present invention, the crossing guidewire can be placed using still another approach, which will sometimes hereinafter be referred to as the "cross and receive" approach. More particularly, with the "cross and receive" approach, a first positioning sheath is passed into the left ventricle via the apical access sheath and its distal end is positioned against the annulus at a first location. Then a first curved tube is advanced out of the first positioning sheath and through the annulus at that first location. Next, a second positioning sheath is passed into the left ventricle via the apical access sheath and its distal end is positioned against the annulus at a second location. Then a second curved tube is advanced out of the second positioning sheath and through the annulus at that second location.

Next, an inflatable funnel is advanced, in a deflated state, through the second curved tube of the second positioning sheath so that the inflatable funnel faces the first curved tube exiting the first positioning sheath. Then the inflatable funnel is inflated so that the mouth of the inflatable funnel faces the first curved tube exiting the first positioning sheath. Next, a guidewire is advanced through the first curved tube of the first positioning sheath, across the left atrium and into the inflatable funnel exiting the second curved tube of the second positioning sheath. The guidewire is advanced down the second curved tube of the second positioning sheath until the distal end of the guidewire emerges at the operative sterile field. The first positioning sheath and its associated annulus-crossing first curved tube are withdrawn, the inflatable funnel is deflated and withdrawn from the second curved tube of the second positioning sheath, and then the second positioning sheath and its associated annulus-crossing second curved tube are withdrawn, leaving the guidewire extending from the apex, across the left ventricle, through one side of the annulus, into the left atrium, through the other side of the annulus, across the left ventricle and back down to the apex.

Once the crossing guidewire has been established, preferably using one of the aforementioned three approaches (i.e., the "cross and snare" approach, the "cross and catch" approach, or the "cross and receive" approach), a spanning implant can be deployed across the annulus of the mitral valve so as to reconfigure the geometry of the mitral valve.

More particularly, the spanning implant comprises a spanning suture having a first end, a second end and a first anchor secured to the first end of the spanning suture. The spanning implant also comprises a second anchor which is fit over the second end of the spanning suture, slid along the spanning suture to an appropriate position and then secured in place, as will hereinafter be discussed.

The spanning implant is preferably deployed in the following manner. First, one end of the crossing guidewire is secured to the second end of the spanning suture. Then the crossing guidewire is used to draw the spanning suture from the apex, across the left ventricle, through one side of the annulus, across the left atrium, through the other side of the annulus, across the left ventricle, and back down to the apex. The crossing guidewire is pulled until the first anchor at the first end of the spanning suture is seated against the annulus, generally disposed in the space between the leaflet insertion and the ventricular wall. The second anchor is then slid onto the second end of the spanning suture and advanced until the second anchor seats against the opposite side of the annulus. Thus, as a result of the foregoing, the first anchor is disposed against the ventricular side of the annulus at a first location, the spanning suture extends through the annulus at that first location, across the left atrium, and through the annulus at a second location, and the second anchor seats against the ventricular side of the annulus at the second location.

Finally, an implant tensioning tool, integrally fitted with a coaxial suture lock, is advanced over the second end of the spanning suture so as to engage the second anchor. The implant tensioning tool is then used to progressively tension the spanning suture, which causes the two sides of the annulus to be drawn together along the line of the spanning suture, until the desired anterior/posterior dimension is achieved for the annulus, whereby to provide the desired reduction in mitral regurgitation. Preferably this tensioning of the spanning suture is done under real-time ultrasound observation. Once the desired mitral reconfiguration has been achieved, the implant tensioning tool is used to lock the second anchor in position on the spanning suture with the coaxial suture lock. This maintains the mitral valve in its reconfigured state. The implant tensioning tool is then removed, and the excess spanning suture remaining proximal to the coaxial suture lock may then be removed (e.g., with a cutoff tool) or terminated to the left ventricular wall.

This foregoing process may then be repeated as needed with other spanning implants so as to effect a complete, effective and structurally durable reconfiguration of the mitral valve. It is anticipated that, in a typical case, two spanning implants will be used to reconfigure the annulus, each anchored in either the anterior or posterior trigone and spanning from the trigone to the posterior annulus, with the anterior trigone connected to the posterior annulus generally in the vicinity of the P1/P2 leaflet intersection, and the posterior trigone connected to a point in the vicinity of the P2/P3 leaflet intersection. It is anticipated that, depending upon the degree of dilation of the mitral annulus, and the specialized anatomical issues of a particular patient, as many as four or five spanning implants may be used to reconfigure the annulus, anchored through the anterior and posterior trigones, or from a more central point along the central fibrous body of the heart, and across and through the posterior annulus.

In one preferred form of the invention, the spanning implant may be deployed from anterior to posterior, i.e., the first, fixed anchor is deployed against the anterior annulus and the second, sliding anchor is deployed against the posterior annulus. However, it is also anticipated that the direction of the spanning implant might be reversed, with the first, fixed anchor deployed against the posterior annulus and the second, sliding anchor deployed against the anterior annulus.

It should be appreciated that the procedure described above has distinct advantages over many alternative approaches. The approach of the present invention can, as described, effect substantial, effectively unlimited reduction of the anterior/posterior dimension of the mitral annulus. Furthermore, the method affords all of the advantages of a minimally invasive procedure.

In one preferred form of the invention, there is provided a method for repairing a mitral valve, the method comprising:

positioning a crossing guidewire across the mitral valve, the crossing guidewire passing through the annulus of the mitral valve at a first location and passing through the annulus of the mitral valve at a second location;

using the crossing guidewire to position a spanning implant across the mitral valve, with the spanning implant extending from the first location to the second location;

anchoring the spanning implant at the first location;

tensioning the spanning implant so as to draw the first location and the second location together; and anchoring the spanning implant at the second location.

In another preferred form of the invention, there is provided apparatus for repairing a mitral valve, the apparatus comprising:

a suture having a first end and a second end, a first anchor secured to the first end of the suture, a second anchor slidably mounted to the second end of the suture, and a coaxial suture lock for locking the second anchor to the suture.

In another preferred form of the invention, there is provided apparatus for repairing a mitral valve, the apparatus comprising:

a crossing guidewire extending from the left ventricle, through the annulus at a first location, into the left atrium, through the annulus at a second location, and into the left ventricle.

In another preferred form of the invention, there is provided apparatus for repairing a mitral valve, the apparatus comprising:

a positioning sheath having a distal end, a proximal end, and a lumen extending therebetween, the positioning sheath being configured to extend across the left ventricle and contact the annulus of the mitral valve at a first location, with the distal end of the positioning sheath set so that the lumen of the positioning sheath is aimed into the left atrium; and a curved tube having a distal end, a proximal end, and a lumen extending therebetween, the curved tube being configured to telescopically extend through the positioning sheath, across the annulus at the first location and present its distal end substantially parallel to the plane of the mitral valve annulus.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 16 is a schematic view showing a spanning implant disposed across the mitral valve, whereby to reconfigure the mitral annulus and thereby reduce mitral regurgitation.

DETAILED DESCRIPTION OF THE PREFERRED EMBODIMENTS

The present invention summarized above may be better understood by reference to the following exemplary description of the preferred embodiments, which should be read in conjunction with the accompanying drawings wherein like reference numbers are used for like parts. The following description of the preferred embodiments, set out below to facilitate the construction and use of an implementation of the present invention, is not intended to limit the present invention, but instead to serve as a particular example thereof so as to facilitate its construction and use. Those skilled in the art should appreciate that they may readily use the conception and specific embodiments disclosed herein as a basis for modifying the method and apparatus disclosed, or designing additional methods and apparatus, for carrying out the same purposes of the present invention. It should be appreciated that such methods and apparatus do not depart from the spirit and scope of the present invention in its broadest form.

Figure 1:
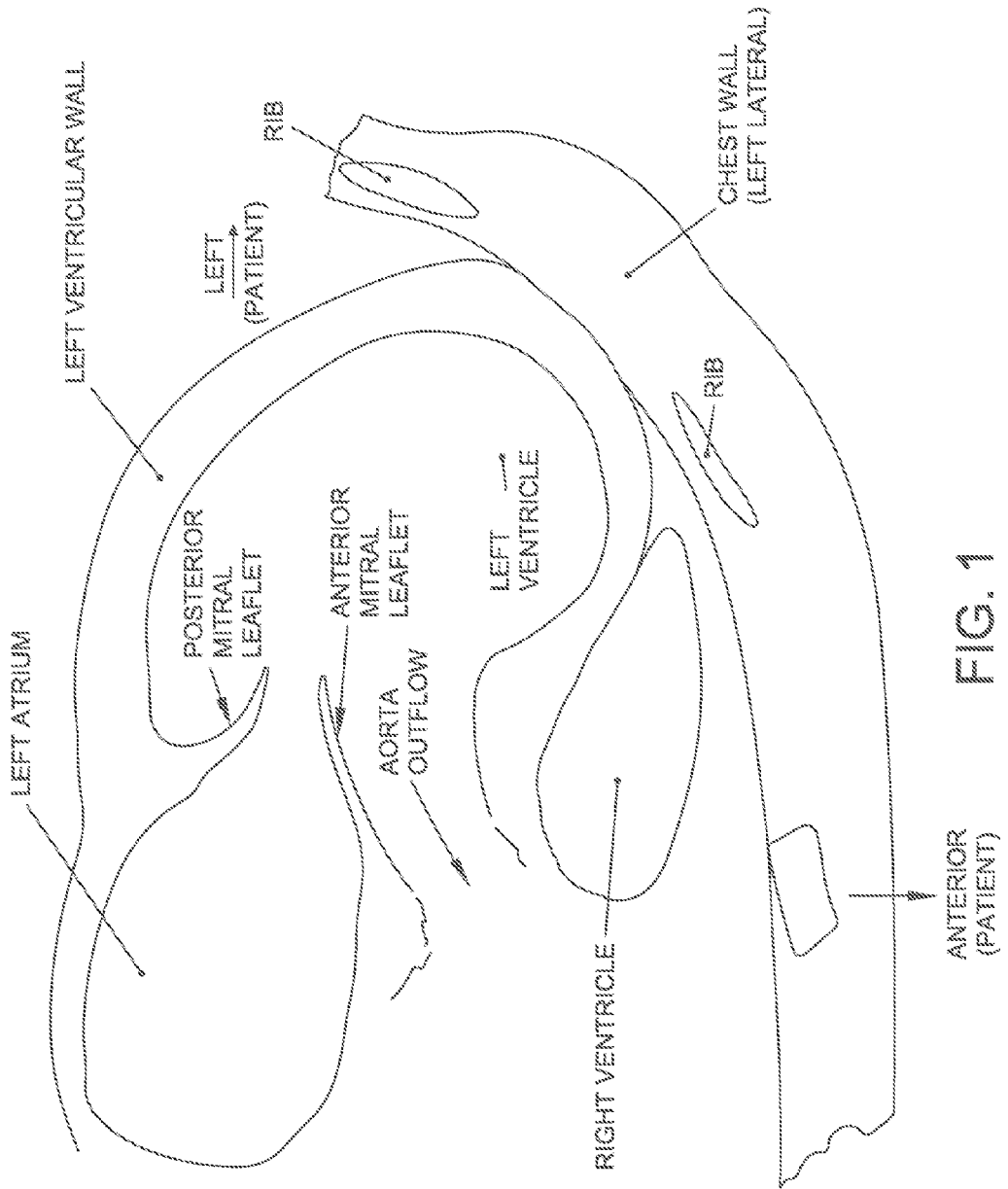
FIG. 1 is a schematic view showing the relevant target anatomy for the method and apparatus of the present invention, with the view being taken along an axial plane through the apex of the left ventricle and the leaflets of the mitral valve.

In accordance with the present invention, the heart may be accessed through one or more openings made by one or more small incisions in a portion of the body proximal to the thoracic cavity, for example, between one or more of the ribs of the rib cage, proximate to the xyphoid appendage, or via the abdomen and diaphragm. This location can be appreciated by viewing the anatomy shown in FIG. 1. Access to the thoracic cavity may be sought so as to allow the insertion and use of one or more thorascopic instruments. Additionally, access to the heart may be gained by direct puncture of the heart from the xyphoid region (i.e., via an appropriately sized needle, e.g., an 18 gauge needle). Access may also be achieved using percutaneous means. Accordingly, the one or more incisions should be made in such a manner as to provide an appropriate surgical field and access site to the heart.

Suitable surgical candidates are identified by reviewing available cardiac imaging which may include, but is not limited to, transesophageal echocardiogram (TEE), transthoracic echocardiogram (TTE), magnetic resonance imaging (MRI), computer tomography (CT), fluoroscopy, chest x-rays, etc. Rendered 3D models of the patient's anatomy may be constructed and reviewed, in addition to reviewing previous imaging of the anatomy, in order to plan device access and the mitral valve repair.

The patient is prepped and placed under anesthesia, and appropriate ultrasound imaging (TEE or TTE) is set up so as to provide real-time assessment of the geometry and function of the mitral valve. The procedure is conducted in a standard cardiac operating room or, optionally, in a hybrid operating room which additionally provides for fluoroscopic imaging. A minimally invasive approach is used to access the thoracic cavity. This minimally invasive approach involves a small incision in the skin between the ribs to expose a surgical field suitable for device access and to provide a purse-string suture for the access site if necessary. Such an incision is typically about 1 cm to about 10 cm in length, or about 3 cm to about 7 cm in length, or about 5 cm in length, and should be placed near the pericardium so as to allow ready access to, and visualization of, the heart.

The planned access point and device orientation is generally determined by pre-procedure imaging and anatomical models, and is confirmed by anatomical landmarks and procedural imaging such as ultrasound and fluoroscopy. Access to the left ventricle of the heart may be made at any suitable site of entry, but is preferably made through a point near to, but not at, the apex of the heart, in a region of diffuse vasculature, so as to avoid coronary arteries, papillary muscles and chordae tendineae. Apparatus orientation is optimized so as to provide access to the applicable target locations of the mitral valve annulus and to minimize the need to manipulate the access site during device use. The apparatus is advanced into the heart through a small incision stabilized by a purse-string suture, a direct puncture of the heart with the apparatus (with or without a purse-string suture), or by a series of devices of increasing diameter (dilators) until the apparatus with the largest diameter is positioned (with or without a purse-string suture) through the wall of the left ventricle. It is thus expected that the generally preferred axis of alignment of the apparatus will be along a central axis defined by the point of access to the left ventricular apex and the centroid of the mitral valve plane.

Transesophageal echocardiography (TEE)(2D or 3D), transthoracic echocardiography (TTE), intracardiac echo (ICE), or cardio-optic direct visualization (e.g., via infrared vision from the tip of a 7.5 French catheter) may be performed to assess the condition of the heart and its valves. A careful assessment is made of the location and type of cardiac dysfunction via conventional echocardiographic means, e.g., TEE or TTE, so as to facilitate planning of the appropriate structural correction to be performed on the mitral valve annulus, whereby to improve mitral valve function and reduce mitral valve regurgitation. The use of TEE, TTE, ICE or the like can also assist in determining if there is a need for adjunctive procedures to be performed on the leaflets and subvalvular structures, and can indicate whether a adjunctive or alternative minimally invasive approach, or direct surgical approach, is advisable.

All of the steps and apparatus described below can be best appreciated by reference to the attached figures. The operative method and preferred apparatus characteristics will now be described, including multiple preferred embodiments of the method and apparatus of the present invention.

1. Left Ventricular Access

Access will generally be effected along the left lateral chest wall between the ribs, either with an initial small surgical exposure cut-down, or via direct percutaneous needle puncture. The choice of the specific access method will generally be guided by imaging and considerations such as possible interference with the lobes of the lung.

Apical access is directed by pre-procedural modeling and imaging, and inter-procedural imaging, as previously described. It is expected that the preferred access location and direction will be along an axis directed centrally through the chosen rib space, left ventricle and mitral valve.

Direct percutaneous left ventricular puncture, with or without supplemental dilation, is effected using standard Seldinger techniques well understood in the surgical arts including, in this specific case, the use of an appropriate left ventricular closure device.

Figure 2:
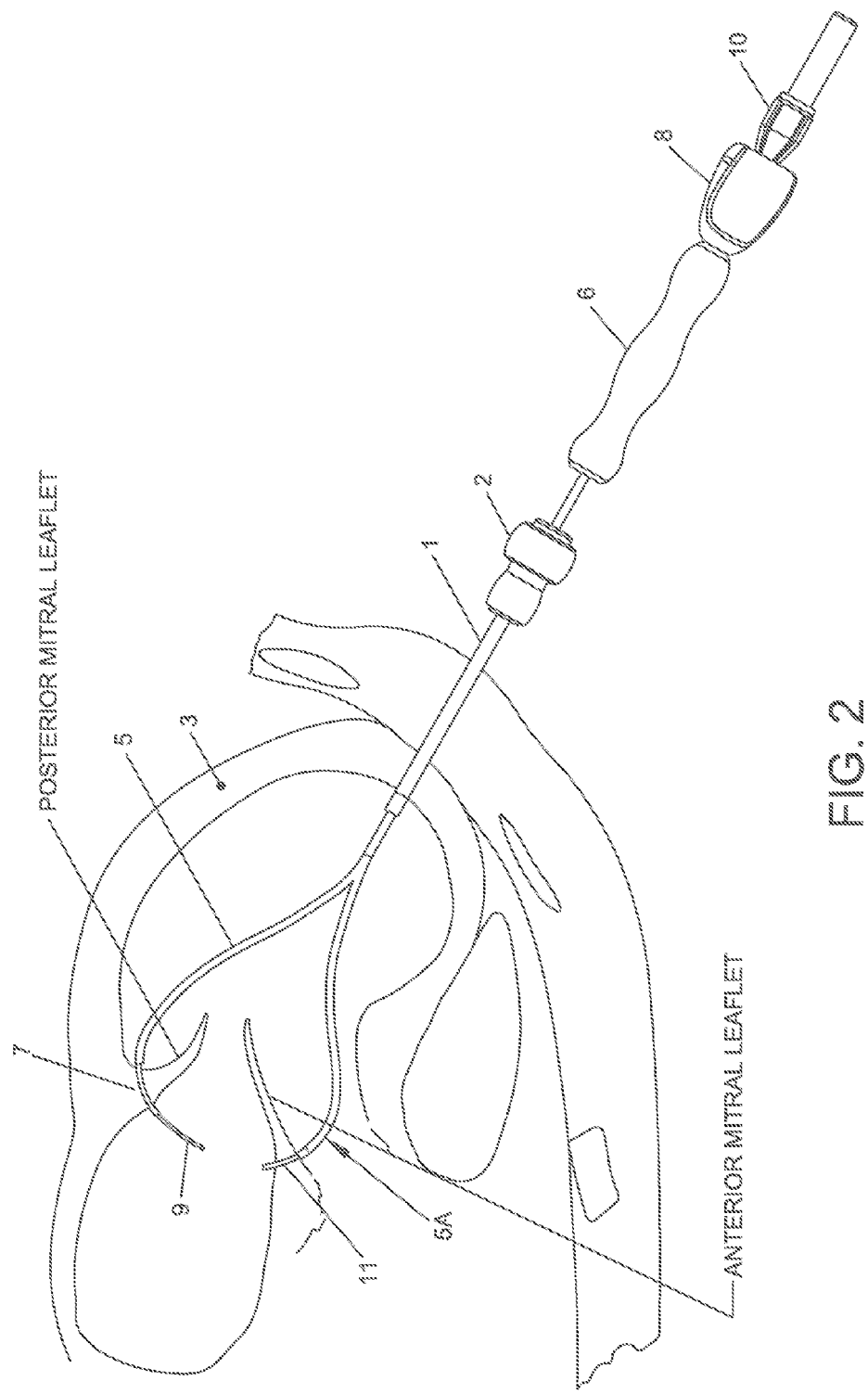
FIG. 2 is a schematic view showing selected apparatus of the present invention in position within the anatomy, with access to the left ventricle having been established with an apical access sheath, and with apparatus for accessing the underside of the posterior mitral annulus and the anterior mitral annulus being shown in position.
Figure 3:
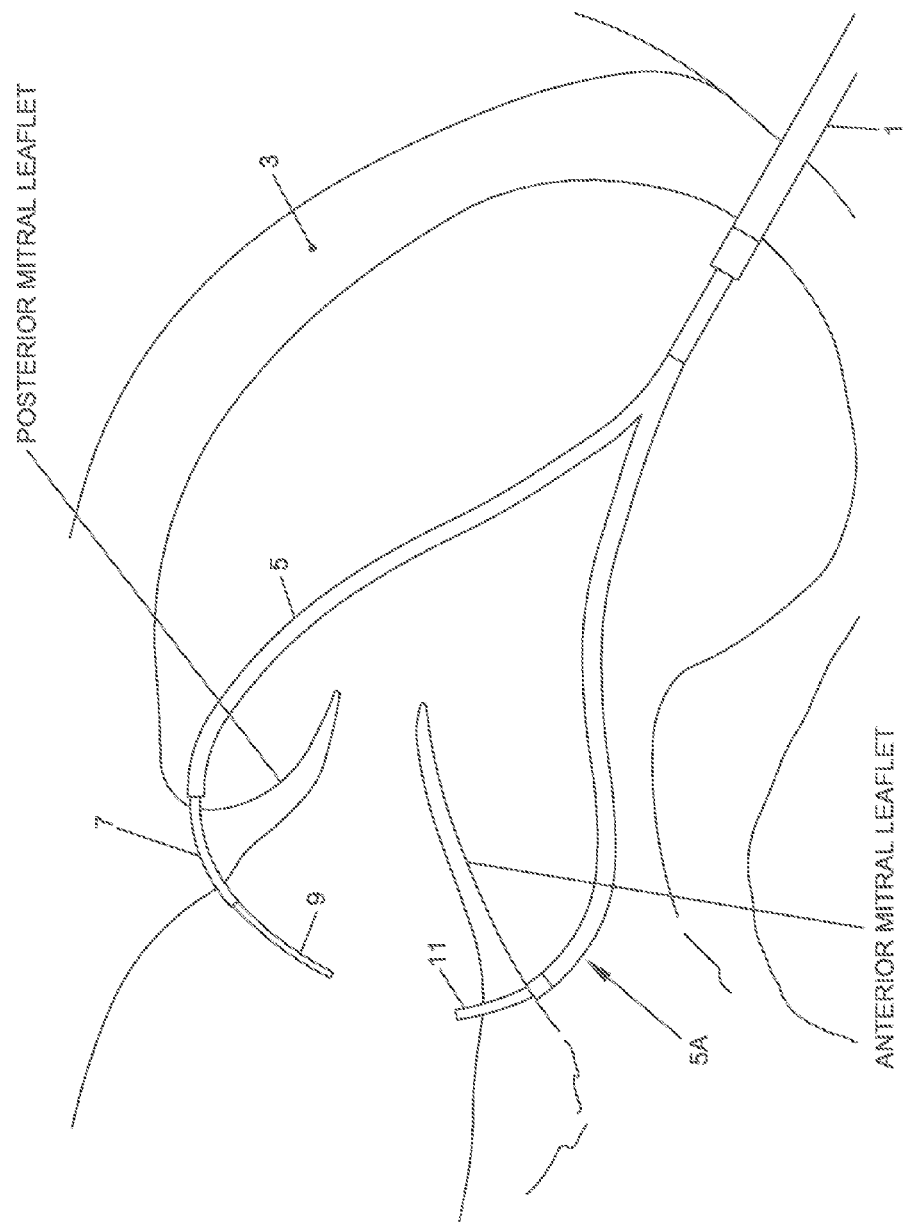
FIG. 3 is a schematic view showing first and second curved tubes crossing the mitral annulus on both the posterior and anterior sides, and with a crossing guidewire emerging from one of the curved tubes.

Following the establishment of left ventricular access, an apical access sheath 1 (FIG. 2), preferably between about 3 cm and about 10 cm long, and between about 2.5 mm and about 4 mm internal diameter, typically fitted with an integral, adjustable internal diameter hemostasis valve 2, and with minimal rigid length, is placed into the left ventricle. FIG. 2 shows apical access sheath 1 and hemostasis valve 2 positioned through the chest wall and through the myocardium 3.

Figure 9:
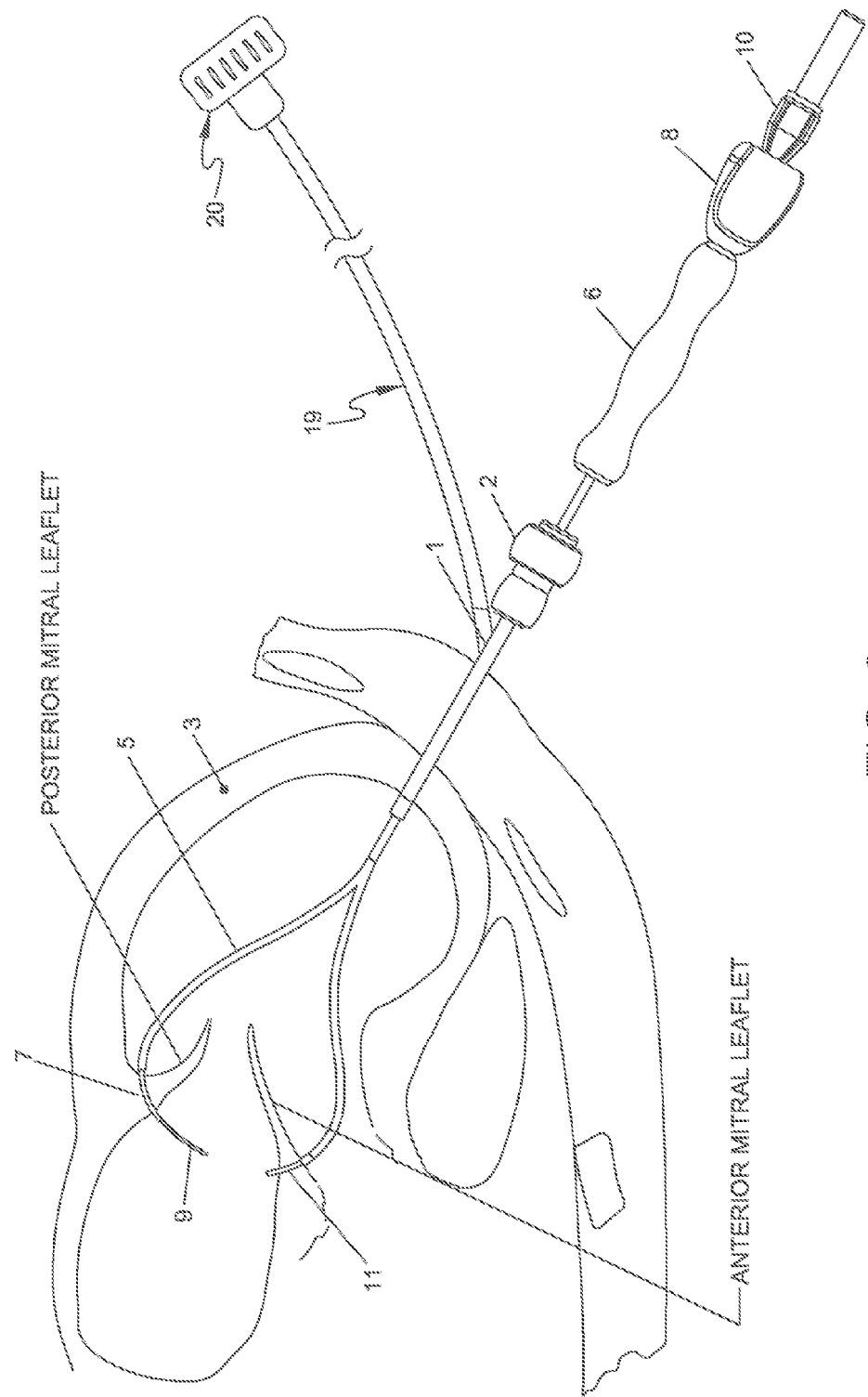
FIG. 9 is a schematic view showing a side port access sheath connected to the apical access sheath.
Figure 10:
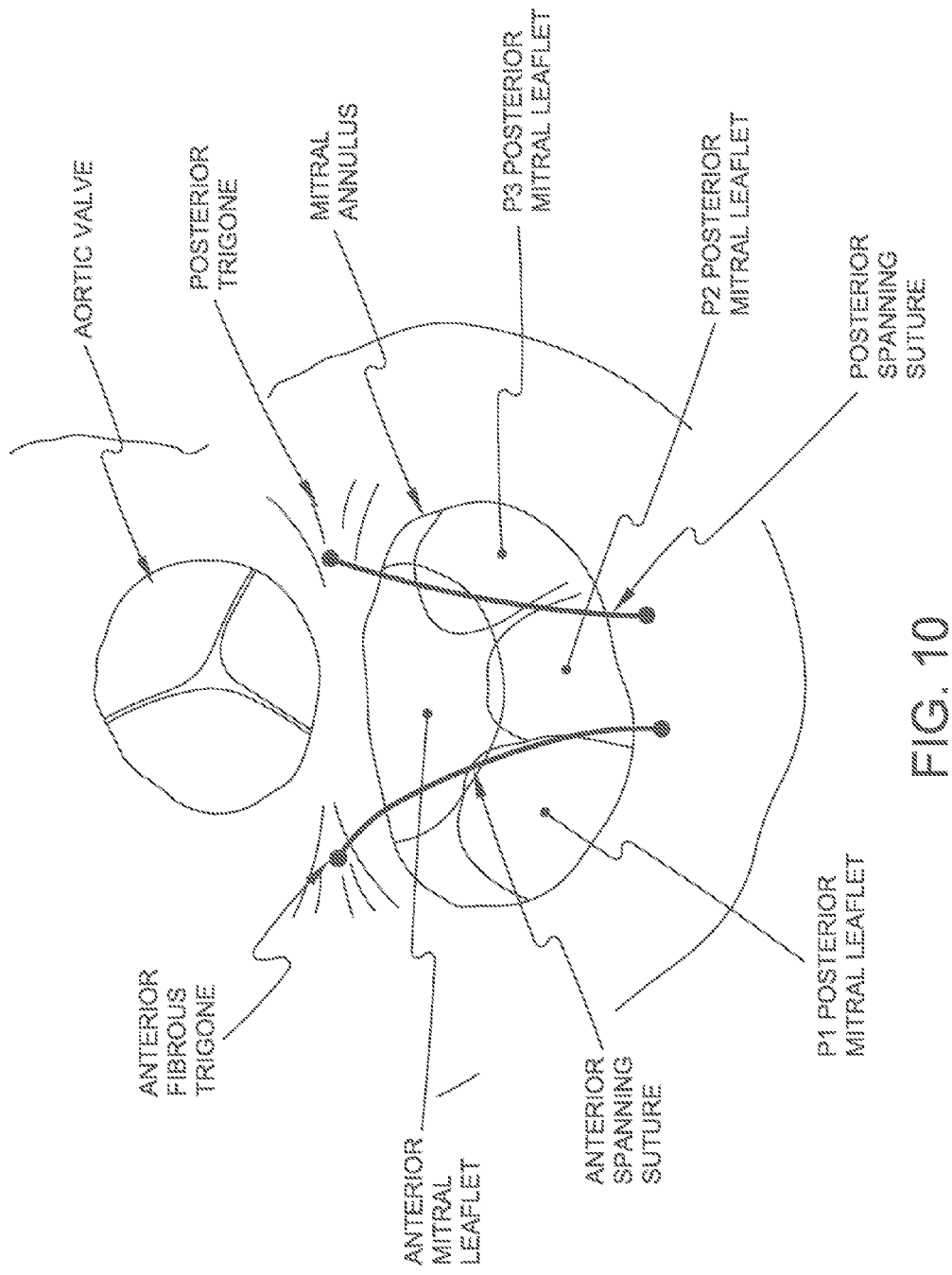
FIG. 10 is a schematic view showing the typical locations for the spanning implants, including the entry points into the fibrous trigones and the posterior mitral annulus.

Alternatively, FIG. 9 shows another preferred embodiment of apical access sheath 1. As seen in FIG. 9, in addition to the access sheath features described above, a second branch or "Y" leg, constituting a side port access sheath 19, is provided to allow for a second independent access path from the operative sterile field into apical access sheath 1. Side port access sheath 19 is preferably also fitted with an integral, adjustable internal diameter hemostasis valve 20, and joins apical access sheath 1 distal to hemostasis valve 2. The provision of side port access sheath 19 allows for more independent manipulation of multiple clinical tools during the procedure, as will be discussed further below.

2. Establishing the Crossing Guidewire by the "Cross and Snare" Approach

One preferred approach for beneficially modifying the mitral annulus employs a novel technique, sometimes herein referred to as the "cross and snare" approach, for safely and accurately establishing a desired suture path across the mitral annulus.

The first tool employed in the "cross and snare" procedure is sometimes referred to herein as the "target and cross tool", or "TCT". The TCT can be prepared in various specific variants depending upon the particular preferred embodiment being implemented. More particularly, the TCT may have a multitude of sizes and shapes, e.g., longer or shorter lengths, more or less curves, more or less curvature, etc., depending on the specific patient (e.g., large patient, small patient, etc.) and anatomy to be targeted (e.g., anterior annulus, posterior annulus, a specific trigone, etc.). Thus, the TCT has a preferred shape to allow the clinician to direct the TCT to a desired location on the underside of the posterior mitral annulus in a precise and controlled fashion. The tool characteristics can also be appreciated by reference to the included figures.

FIG. 2 shows a TCT comprising a first positioning sheath 5 and its steering handle 6. First positioning sheath 5 is advanced through apical access sheath 1, through the left ventricle, and into contact with a desired location beneath the posterior side of the mitral annulus. First positioning sheath 5 is generally of low profile, typically 7 French or less. First positioning sheath 5 may include the option for either (i)

passive re-shaping by the clinician by careful bending (e.g., in the manner often applied to interventional tools), or (ii) by active tip control.

Still looking now at FIG. 2, a first curved tube 7 is slidably disposed within first positioning sheath 5. First curved tube 7 includes a handle 8. First curved tube 7 is preferably between about 19 gauge and 23 gauge, and is also pre-shaped in a curvilinear fashion so as to allow it to pass through the annulus and arc towards the central open area of the left atrium (see FIG. 2). First curved tube 7 may either be sharp, and thus passed through the annular tissue under direct pressure, or it may be smooth-tipped and serve to guide an internally-positioned RF puncture wire (either custom made or commercially available). If first curved tube 7 is fitted with an internally-positioned RF puncture wire, such wire may be activated with RF energy and advanced through the annulus. First curved tube 7 can then be advanced so as to track along the internally-positioned RF puncture wire in a standard manner while dilating the tissue to achieve passage. Such a configuration has the advantage of stretching the tissue around the internally-positioned RF puncture wire as the first curved tube 7 advances, and thus can be expected to leave a smaller hole upon removal. The advancement of first curved tube 7 and the internally-positioned RF puncture wire may be done simultaneously or, alternatively, the internally-positioned RF puncture wire can be advanced independently of first curved tube 7.

As can be appreciated from the figures, curving first curved tube 7 in the range of a radius of curvature of about 6-20 mm will provide for a crossing path that curves through the fibrous annulus from the left ventricle side into the left atrium while minimizing the possibility of first curved tube 7 puncturing the left atrium. See FIG. 2. The curvature can be readily observed and oriented using fluoroscopy, echocardiography, and pre-planning CT images. First curved tube 7 may be made of Nitinol or other superelastic material to facilitate the retention of a desired, pre-curved shape as first curved tube 7 is advanced and retracted into first positioning sheath 5. First curved tube 7 may also be selectively constructed out of coiled or laser cut material so as to selectively add a greater range of shapeability or to reduce stiffness. Similarly, a curved internally-positioned RF puncture wire fitted to first curved tube 7 may also be fabricated from Nitinol or other superelastic material.

First curved tube 7 includes a guidewire lumen within the tube, which may first carry the aforementioned internally-positioned RF puncture wire, and later carries a first guidewire 9 (see FIG. 2), which may be either a conventional guidewire or a custom-curved guidewire. The lumen in first curved tube 7 is preferably sized to allow passage of conventional coronary guidewires, such as guidewires having diameters of 0.014 inch, 0.025 inch or 0.035 inch.

In accordance with the present invention, first positioning sheath 5 is positioned so as to contact the annulus in the desired location on the left ventricle side of the posterior annulus, and oriented so as to point into the left atrium. The targeting and shaping of first positioning sheath 5 can be readily appreciated with reference to FIG. 2. The orientation of first positioning sheath 5 is facilitated by the orientation of steering handle 6 and also referenced to real-time echocardiography and fluoroscopy, as well as referenced to previously-recorded computed tomography data. The shape of first positioning sheath 5, and the single, low profile nature of its construction, allows the clinician to safely and controllably direct first positioning sheath 5 to any point beneath the mitral annulus and orient first positioning sheath 5 such that the crossing by first curved tube 7 will occur across the annulus approximately along the intended final line of travel of the spanning implant.

There are various possible approaches to effecting the controlled and safe crossing of first curved tube 7 into the left atrium, the principles of which are generally adapted from well-understood clinical techniques. The simplest approach is to use a sharpened or beveled edge on first curved tube 7, and pressure on the proximal end of handle 8 of first curved tube 7, to cross the annulus and enter the left atrium. In this particular setting, this approach has the disadvantage of causing the release of potential embolic debris, and being less controlled, inasmuch as more pressure might be required to penetrate the annulus and also raises the possibility of damaging surrounding anatomy if first curved tube 7 should plunge forward as it exits the far side of the annulus. Alternatively, first curved tube 7 may be provided with the aforementioned internally-positioned RF puncture wire so as to facilitate passage of first curved tube 7 through the mitral annulus.

First curved tube 7 is advanced (with RF assistance if necessary) into the left atrium with operator-controlled pressure and forward motion. See FIG. 2. Handle 6 on first positioning sheath 5, and handle 8 on first curved tube 7, are presented and labeled so as to give the operator good indication of the orientation and degree of advancement of first curved tube 7 vis-à-vis first positioning sheath 5.

After first curved tube 7 has been advanced through the mitral annulus, first guidewire 9 (controlled by a guidewire handle 10) is then advanced through first curved tube 7 and into the left atrium, to be positioned visibly and stably in the left atrium under the control of guidewire handle 10. See FIG. 2. If desired, first guidewire 9 may be a conventional guidewire or, alternatively, first guidewire 9 may be an RF guidewire, in which case the functions of the aforementioned internally-positioned RF puncture wire and first guidewire 9 may be combined. In other words, where first guidewire 9 is an RF guidewire, first guidewire 9 may first be used as the internally-positioned RF puncture wire to facilitate passing first curved tube 7 through the mitral annulus, and thereafter used for establishing the crossing guidewire, as will hereinafter be discussed.

Once first guidewire 9 has been advanced through first curved tube 7 and into the left atrium (FIG. 2), first positioning sheath 5 is then retracted, leaving first curved tube 7 and first guidewire 9 in position.

Figure 11:
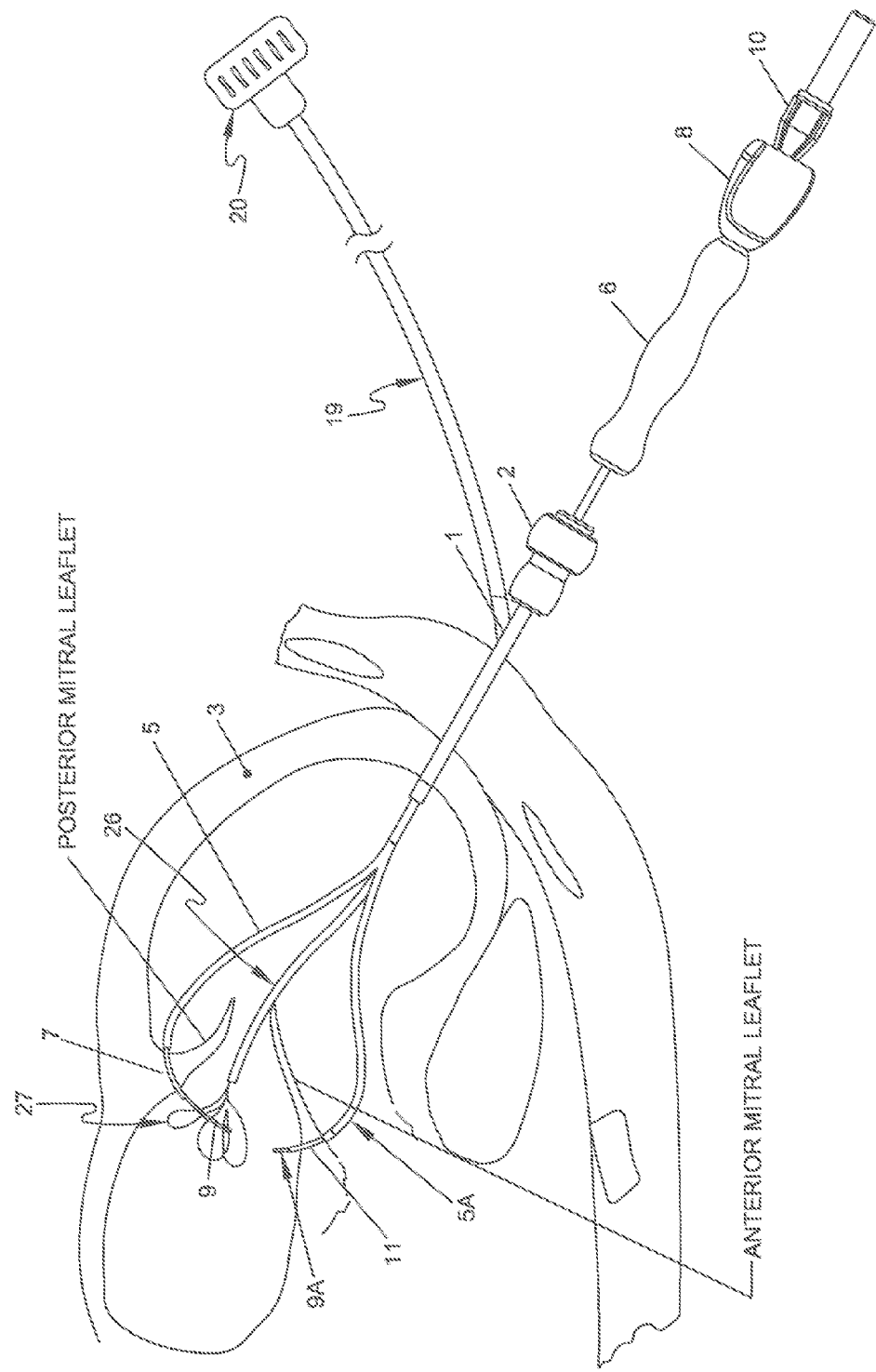
FIG. 11 is a schematic view showing the aforementioned center sheath and its associated snare advanced through the side port access sheath, through the left ventricle, across the mitral leaflets and into the left atrium.

Next, and looking now at FIG. 11, a second TCT, comprising a second positioning sheath 5A, is used to place a second curved tube 11 and a second guidewire 9A through the opposite (i.e., anterior) side of the annulus, using an identical technique.

Once second curved tube 11 and second guidewire 9A are positioned through the second (i.e., anterior) side of the mitral annulus, conventional interventional tools may be employed to complete the establishment of a crossing guidewire across the annulus.

In one preferred form of the invention, and looking now at FIG. 11, a center sheath 26 is advanced through apical access sheath 1, between the mitral valve leaflets and into the left atrium. Then a snare 27 (e.g., a conventional, low-profile interventional snare) is advanced through center sheath 26 and into the left atrium so that it sits between first guidewire 9 and second guidewire 9A. Such coronary snares are well-known in the art of interventional cardiology. Preferably snare 27 is introduced into apical access sheath 1 by advancing the snare through side port access sheath 19 of apical access sheath 1.

Snare 27 is advanced through center sheath 26 and used to capture first guidewire 9. See FIG. 11. Snare 27 is then fully retracted back through center sheath 26 and apical access sheath 1 until the distal end of first guidewire 9 is drawn through apical access sheath 1 and out into the operative sterile field.

Snare 27 is then advanced back down apical access sheath 1 and center sheath 26 while first guidewire 9 remains in the lumen of center sheath 26. Snare 27 is then used to capture second guidewire 9A. Then snare 27, carrying the captured second guidewire 9A with it, is fully retracted down center sheath 26 and apical access sheath 1, causing the distal end of second guidewire 9A to be drawn through apical access sheath 1 and out into the operative sterile field.

The distal tips of the two guidewires are then joined, or "docked", in the operative sterile field.

Note that, as an alternative to the foregoing sequence in which both first guidewire 9 and second guidewire 9A are disposed in the left atrium before they are captured by snare 27, first positioning sheath 5 and first curved tube 7 could be used to pass first guidewire 9 across the annulus on one side of the mitral valve, first guidewire 9 could then be snared by snare 27 and retracted out to the operative sterile field by snare 27, then second positioning sheath 5A and second curved tube 11 could be used to pass second guidewire 9A through the opposite side of the mitral annulus, snare 27 could be used to capture the distal end of guidewire 9A and bring it out to the operative sterile field, and then the distal ends of the two guidewires 9, 9A could be joined in the operative sterile field.

Thereafter, the joined distal ends of guidewires 9, 9A are drawn back through apical access sheath 1 and center sheath 26, crossing the left ventricle, so that the joined distal ends of guidewires 9, 9A are located in the left atrium.

As a result of the foregoing, a continuous guidewire path (i.e., a "crossing guidewire") is established, traveling from the left ventricle, through the posterior annulus, across the left atrium, back through the anterior annulus, and then out through the left ventricle, with the continuous guidewire path extending out to the operative sterile field through apical access sheath 1.

3. Establishing the Crossing Guidewire by the "Cross and Catch" Approach

An alternative approach for establishing the crossing guidewire across the mitral annulus (and hence establishing a desired suture path across the mitral annulus) is sometimes hereinafter referred to as the "cross and catch" approach. With this alternative approach, the same operative objective (i.e., the establishment of the crossing guidewire) is achieved using a different combination of steps and apparatus, in particular using a first "target and cross tool", sometimes hereinafter referred to as TCT1, and a second "target and cross tool", sometimes hereinafter referred to as TCT2, as described below.

TCT1 is reinforced for pushability and proximally shapeable, and preferably comprises the following three elements, as follows:

(i) TCT1 comprises a low profile, approximately 6 French first positioning sheath 5 (FIG. 4) having a through lumen and a steering handle 6. First positioning sheath 5 is sufficiently stiff to allow stable placement of the distal tip of first positioning sheath 5 against target locations on the mitral annulus. First positioning sheath 5 may be shaped in various ways to best match the target anatomy, either as supplied or as modified in the field by the clinician.

(ii) TCT1 also comprises a first curved tube 7, approximately 19-23 gauge in diameter, with handle 8, which is fitted in the lumen of first positioning sheath 5. First curved tube 7 is typically fitted with either a sharpened piercing tip or a smooth tip intended to be used in conjunction with an RF puncture wire of the type discussed above.

Figure 5:
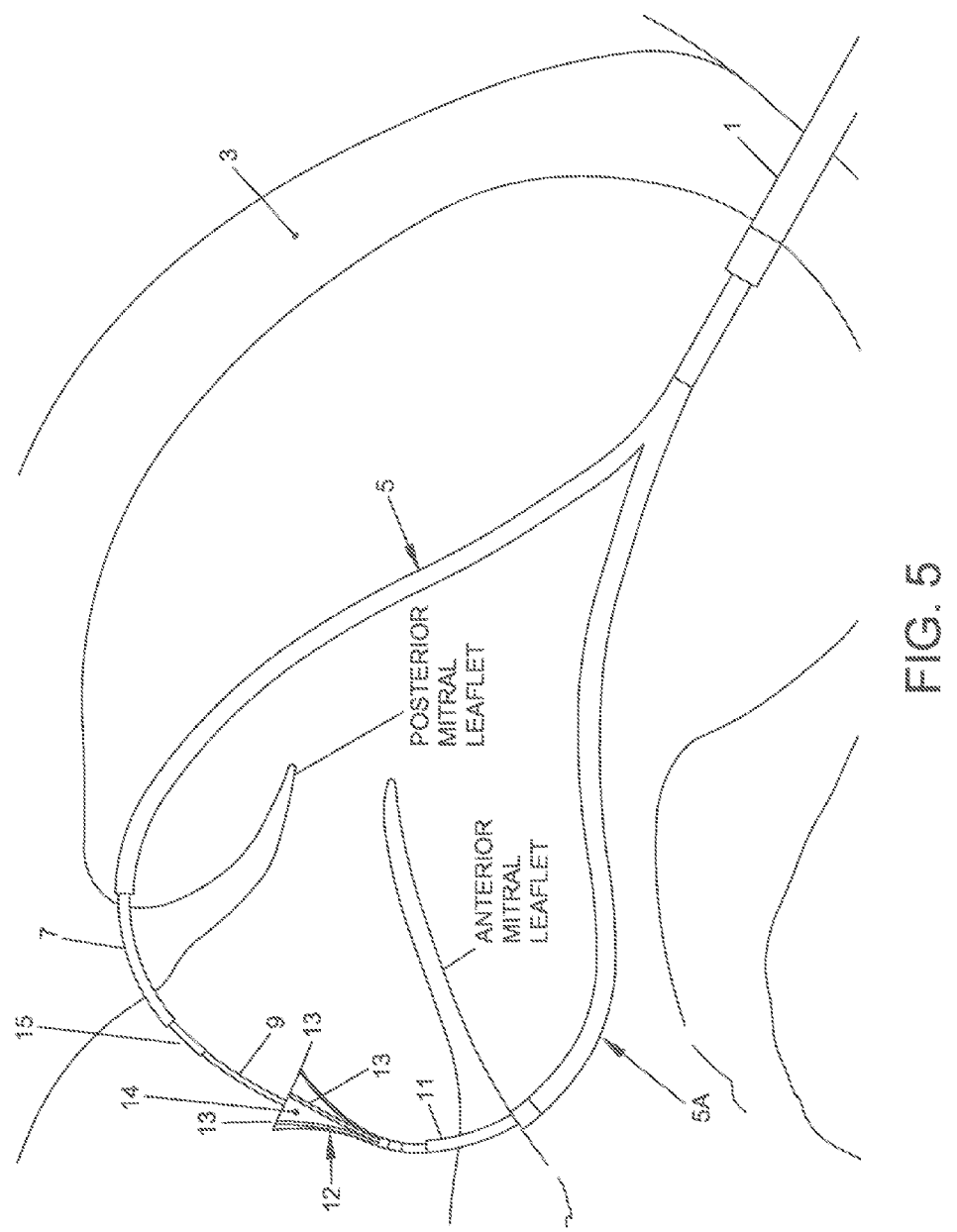
FIG. 5 is a schematic view showing further details of the funnel-shaped snare deployed in the left atrium from the anterior side, and the crossing guidewire deployed in the left atrium from the posterior side.

(iii) TCT1 also comprises a steering tube 15 (FIG. 5). Steering tube 15 is disposed within first curved tube 7 and may be fabricated from Nitinol or another highly elastic material. Steering tube 15 is curved at least as tightly as the distal aspect of first curved tube 7. Steering tube 15 optionally provides for more precise manipulation of a guidewire 9 (FIG. 5) into funnel-shaped snare 12 of TCT2, as will be described below.

Figure 4:
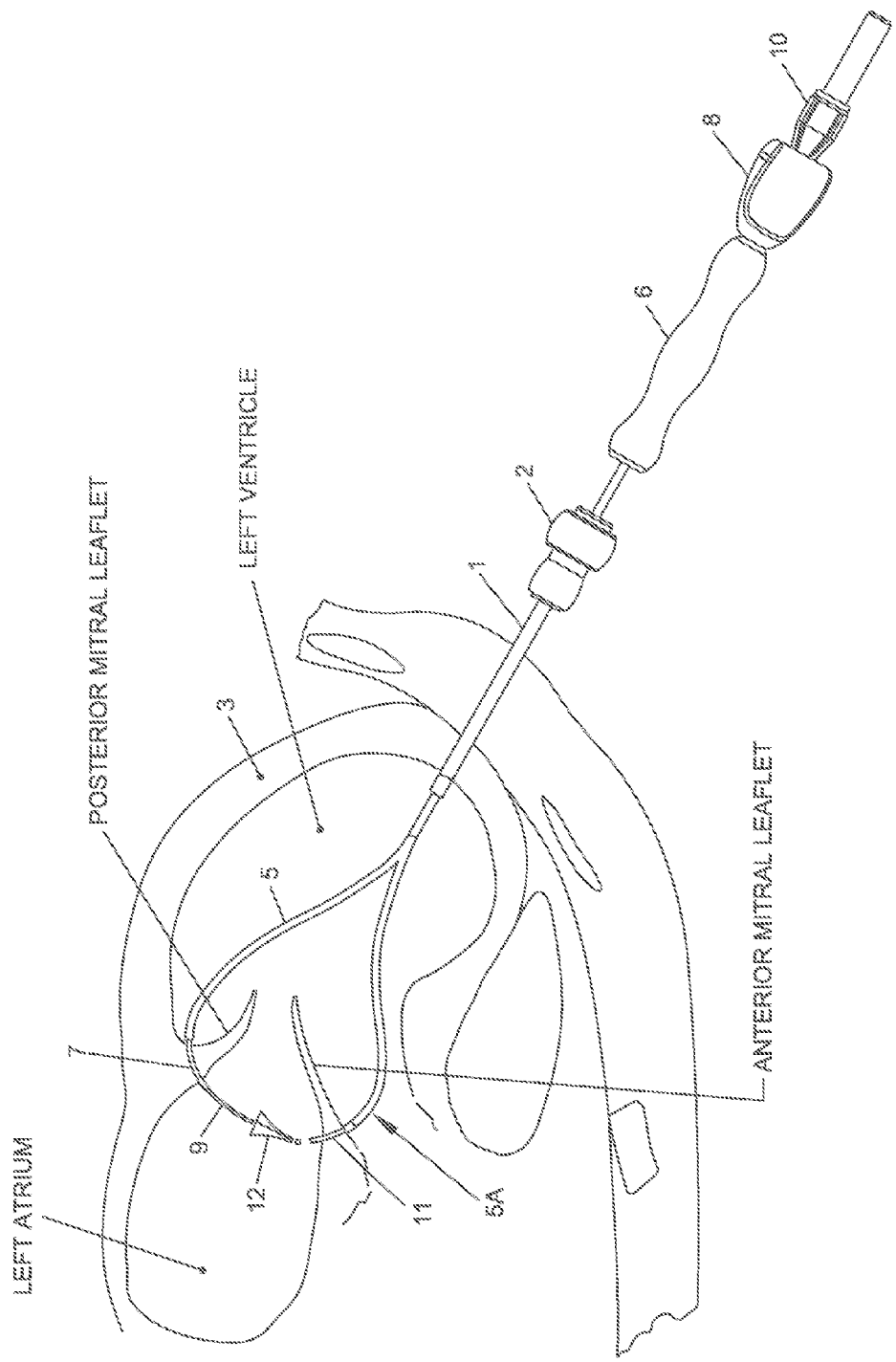
FIG. 4 is a schematic view showing a funnel-shaped snare deployed in the left atrium from the anterior side, and a crossing guidewire deployed in the left atrium from the posterior side.

TCT2 is reinforced for pushability and proximally shapeable and steerable. TCT2 preferably comprises three main elements, as follows:

(i) TCT2 comprises a low-profile, approximately 6 French or approximately 7 French second positioning sheath 5A (FIG. 5) having a through lumen and a steering handle similar to the aforementioned steering handle 6 of first positioning sheath 5. Second positioning sheath 5A of TCT2 is shaped as shown in FIGS. 4 and 5 so that it can be readily directed within the left ventricle to positions on the ventricular side of the mitral annulus.

(ii) TCT2 also comprises a second curved tube 11 (FIGS. 4 and 5) of approximately 19 gauge or approximately 20 gauge, with a steering handle similar to the aforementioned steering handle 8 of first curved tube 7. Second curved tube 11 is slidably disposed in the lumen of second positioning sheath 5A and can be controllably advanced through the annular tissue under the control of its steering handle.

(iii) TCT2 also comprises a funnel-shaped snare 12 (FIGS. 4 and 5) of approximately 0.035 inch outer diameter in a collapsed, undeployed state and fitted within the lumen of second curved tube 11. Funnel-shaped snare 12 passively collapses when travelling through the 0.035 inch lumen of second curved tube 11 and then, when advanced into the left atrium, passively expands into an outwardly directed funnel as shown in FIGS. 4 and 5. In one preferred embodiment, the funnel-shaped snare is fabricated from elastic stiffening ribs 13 such as might be fabricated from Nitinol or another highly elastic material, and an elastomer web 14 which fills out the spaces between the stiffening ribs 13 of funnel-shaped snare 12.

To effect the "cross and catch" approach, TCT1 is positioned so as to contact one side of the annulus in a desired location and oriented so as to point into, and across, the left atrium as described previously and shown in the figures. More particularly, as seen in FIGS. 4 and 5, first positioning sheath 5 is advanced against the ventricular side of the posterior annulus, and then first curved tube 7 is advanced (with RF assistance if necessary) into the left atrium so that the outlet of first curved tube 7 is oriented generally parallel to the mitral annulus plane and oriented by rotation so as to point at the opposite planned anchor point (see below).

A guidewire 9 is advanced through first curved tube 7 and into the left atrium. Steering tube 15 may also, optionally, be advanced coaxially over guidewire 9.

First positioning sheath 5 of TCT1 is then retracted from the left ventricle, leaving first curved tube 7 and guidewire 9 in place, with their distal aspects located in the left atrium. Steering tube 15 may also, optionally, remain in position.

TCT2 is then used to similarly position second curved tube 11 and funnel-shaped snare 12 through the opposite side of the annulus, again oriented to point generally in the direction of the opposite anchor point established by TCT1. More particularly, second positioning sheath 5A is advanced against the ventricular side of the anterior annulus, and then second curved tube 11 of TCT2 is advanced (with RF assistance if necessary) into the left atrium so that the outlet of second curved tube 11 is generally parallel to the mitral annulus plane and oriented by rotation so as to point at the opposite anchor point established by TCT1. See FIGS. 4 and 5.

Second positioning sheath 5A of TCT2 is then retracted, leaving second curved tube 11 and funnel-shaped snare 12 in position. The opposing guidewire 9 is then advanced into funnel-shaped snare 12. Then the funnel-shaped snare 12 is retracted into second curved tube 11 so that it collapses inwardly on guidewire 9, thereby establishing a positive grip on guidewire 9 (i.e., as the funnel-shaped snare is compressed upon recapture within second curved tube 11).

It will be appreciated that the orientations of TCT1 and TCT2, the first and second curved tubes 7 and 11, guidewire 9, and funnel-shaped snare 12 can be manipulated by advancing or rotating, using techniques familiar to those skilled in the art of interventional cardiology, so as to ensure proper docking of guidewire 9 with funnel-shaped snare 12.

Using funnel-shaped snare 12, the distal end of captured guidewire 9 is retracted by pulling second curved tube 11 proximally until the assembly has been withdrawn out of the anatomy into the operative sterile field, whereby to complete deployment of the crossing guidewire via the "cross and catch" approach. Alternatively, funnel-shaped snare 12 may be employed completely passively, i.e., guidewire 9 is advanced into funnel-shaped snare 12 and, by conventional rotation and pressure, advanced down second curved tube 11 until the distal end of the guidewire reaches the operative sterile field travelling retrograde through the inner lumen of funnel-shaped snare 12. In either case, a continuous guidewire path (i.e., the crossing guidewire) is established across the left atrium. In other words, using the aforementioned "cross and catch" approach, the crossing guidewire is established across the left atrium.

4. Establishing the Crossing Guidewire by the "Cross and Receive" Approach

Another alternative approach for establishing a crossing guidewire across the mitral annulus is sometimes hereinafter referred to as the "cross and receive" approach. This alternative approach is effected using a first "target and cross tool", sometimes referred to herein as TCT3, and a second "target and cross tool", sometimes referred to herein as TCT4, as described below.

The key features of TCT3 and TCT4 will first be described, and then their sequence of use will be addressed.

TCT3 (FIGS. 6-8) preferably comprises three major elements, as follows:

(i) TCT3 comprises a 6 French reinforced first positioning sheath 5 with a lumen extending therethrough, curved distal and middle sections, and a steering handle 6. First positioning sheath 5 is shaped so as to reach from the entry point of apical access sheath 1 near the apex of the left ventricle to locations on the mitral annulus; the distal section of first positioning sheath 5 is curved so that the line of action of the exit of the sheath is oriented into the left atrium over a wide range of apical access locations and left ventricular anatomies.

(ii) TCT3 also includes an advanceable first curved tube 7 made of Nitinol and having a curved distal section, generally about 19 gauge to 20 gauge in diameter, with a 0.035 inch lumen, and a proximal handle 8. First curved tube 7 is slidably disposed within first positioning sheath 5. The distal section of first curved tube 7 is curved so that, as it is advanced out of first positioning sheath 5, its exit may be controllably oriented towards the opposite side of the annulus. Nitinol tubing is generally preferred for this application because the curvature of the distal tip may not otherwise be maintained as it is manipulated through the shaped sections of first positioning sheath 5. First curved tube 7 is intended to provide a crossing lumen through the mitral annulus, as will hereinafter be discussed.

(iii) Fitted within first curved tube 7 is an innermost steering tube 15. Steering tube 15 is also preferably made of Nitinol, with a curved distal section, <0.035 inch outside diameter, an internal 0.014 inch lumen, and a proximal handle. The distal section of steering tube 15 is curved (differentially from the first curved tube 7) so that as steering tube 15 is advanced out of first curved tube 7, its exit may be oriented toward the opposite side of the annulus. Nitinol tubing is generally preferred for this application due to its superelastic properties, which will help ensure that the curvature of the distal tip will be maintained as it is manipulated through the shaped sections of first curved tube 7.

Figure 6:
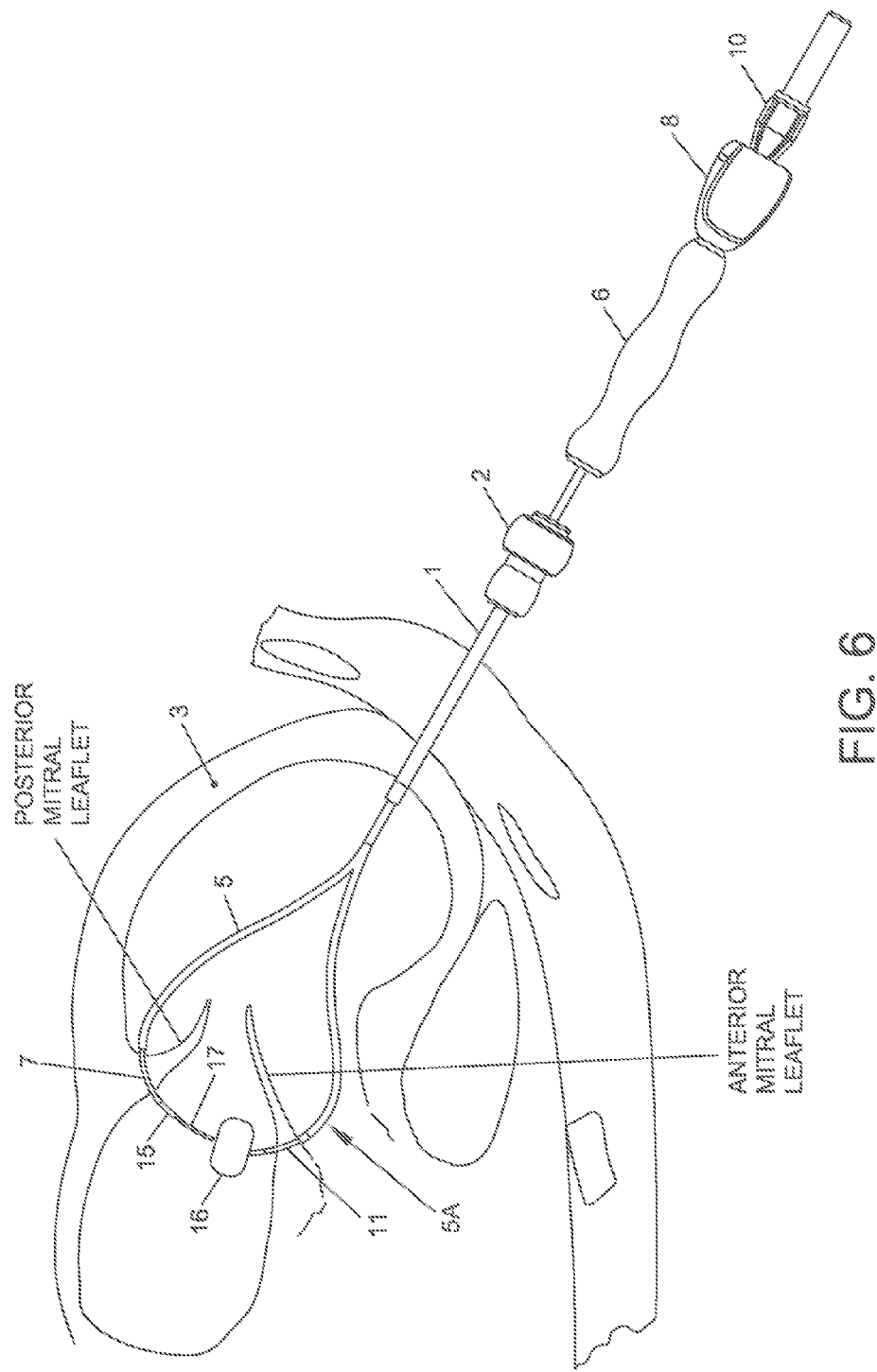
FIG. 6 is a schematic view showing an inflatable funnel deployed in the left atrium from the anterior side, and the crossing guidewire deployed in the left atrium from the posterior side.
Figure 7:
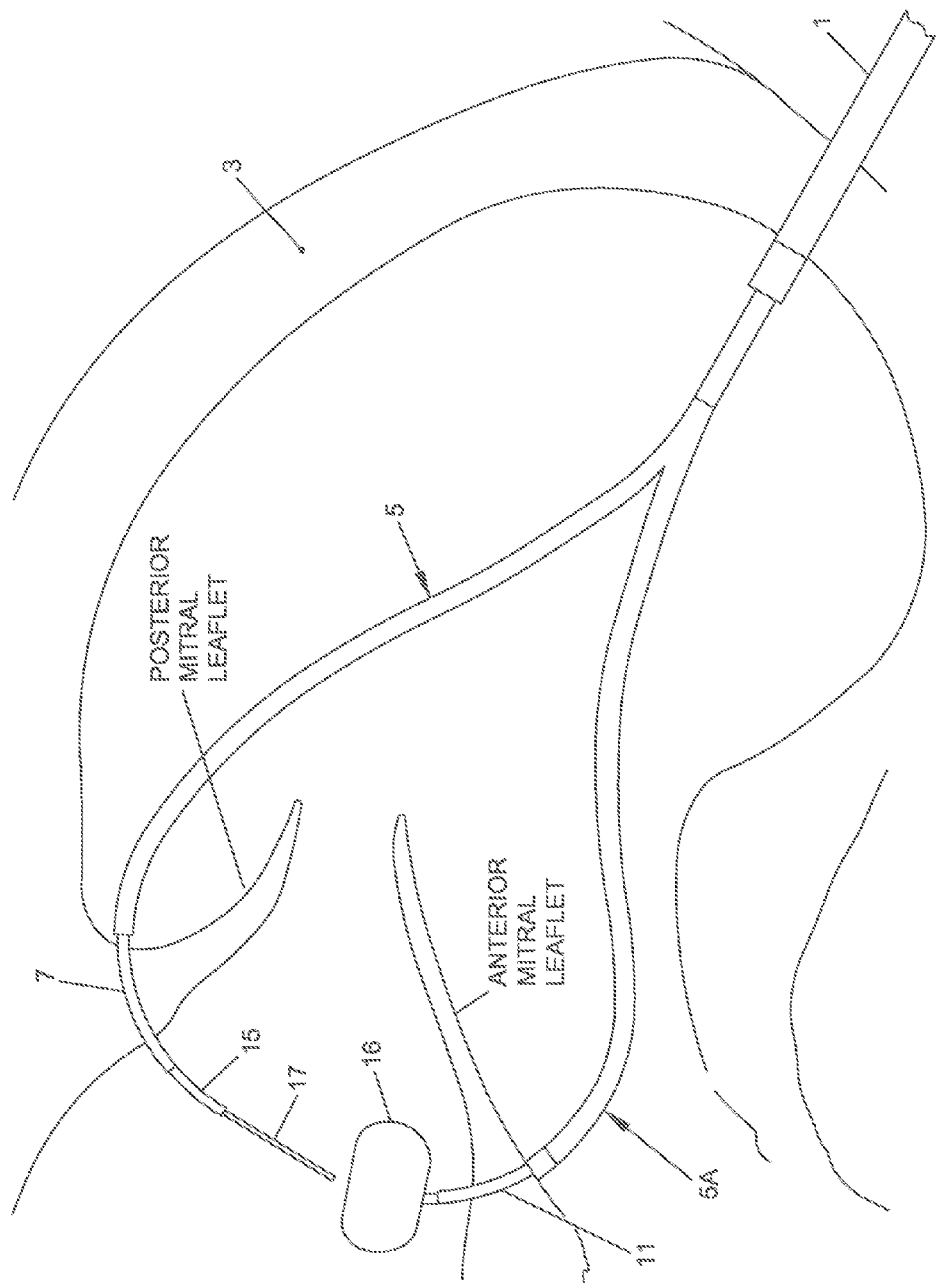
FIG. 7 is a schematic view showing further details of the inflatable funnel deployed in the left atrium from the anterior side, and the crossing guidewire deployed in the left atrium from the posterior side.
Figure 8:
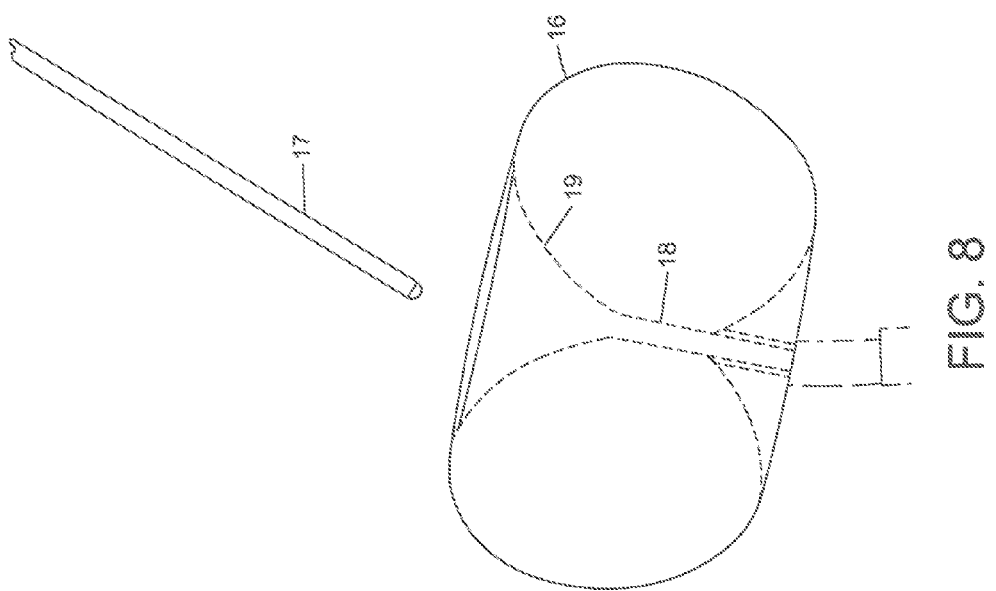
FIG. 8 is a schematic view showing further details of the inflatable funnel.

TCT4 is best seen in FIGS. 6-8 and comprises three major elements as follows:

(i) TCT4 comprises an approximately 6 French second positioning sheath 5A having an interior lumen extending there through, curved distal and middle sections, and a handle similar to the aforementioned steering handle 6. Second positioning sheath 5A is shaped so as to extend through apical access sheath 1 (placed in the apex of the left ventricle) and from there to reach locations on the mitral annulus. In the preferred embodiment, the distal section of second positioning sheath 5A is curved so that the exit of the second positioning sheath is oriented into the left atrium over a wide range of apical access locations and left ventricular anatomies. Second positioning sheath 5A may be re-shapeable by various means including bending, and/or several alternative shapes may be provided so as to account for varying patient size and anatomy.

(ii) TCT4 also comprises a second curved tube 11 (FIGS. 6-8) which is disposed within second positioning sheath 5A. Second curved tube 11 is preferably made of Nitinol and, in a preferred embodiment, fitted with a progressively curved distal section, of 19 gauge or 20 gauge diameter, with an inner lumen of approximately 0.035 inch, and a handle similar to the aforementioned handle 8. The distal section of the second curved tube 11 is curved so that, as it is advanced out of second positioning sheath 5A, its exit may be oriented toward the opposite side of the mitral annulus, and also afford control of the elevation angle of the most distally-advanced aspect of second curved tube 11. Nitinol is generally preferred for this application inasmuch as the range of preferred curvatures of the distal tip may not be maintained as it is manipulated and advanced through the curved sections of second positioning sheath 5A. The distal aspect of second curved tube 11 may be finished to a conventional needle-sharp condition, thus facilitating controlled advance of second curved tube 11 through annular tissue by pushing. Alternatively, the distal aspect of second curved tube 11 may be finished square and smooth, and employed in combination with a conventional, flexible RF-assisted puncture wire or a custom RF-assisted puncture wire of matched-curve construction. In the case of a RF assisted puncture wire, the RF puncture wire may be independently advanced through the annulus and then second curved tube 11 advanced over the RF puncture wire, thus allowing second curved tube 11 to be guided (or "track") over the RF puncture wire along the preferred path.

(iii) TCT4 also comprises an inflatable funnel 16 (FIGS. 6-8). Inflatable funnel 16 is configured with novel features beneficial to the performance of the "cross and receive" approach. Inflatable funnel 16 could, alternatively, be replaced by a Nitinol shape memory element with a self-expanding mesh structure, either with/without a polymer covering, depending upon the fineness of the Nitinol mesh and the desired mating guidewire. The key features of inflatable funnel 16 are as follows:

(a) In the anticipated preferred embodiment, inflatable funnel 16 can be advanced and retracted through an approximately 0.035 inch lumen, with inflatable funnel 16 deflated during advancement and removal. Inflatable funnel 16 is equipped with a 0.014 inch lumen.

(b) The main shaft of inflatable funnel 16 is preferably reinforced with either steel or Nitinol tubing, or a braided composite tube, so as to provide for positive torsional and advance/retraction control during positioning.

(c) In a preferred embodiment, inflatable funnel 16 comprises a unique elastomeric distal balloon with several important properties. The inflated shape of the distal balloon is such that when inflated, it projects distally beyond the end of second curved tube 11 with an overall diameter of approximately 10 mm. Viewed on end, the distal face of the balloon forms a funnel-like mouth 19 (FIG. 8) with diameter of approximately 6 mm of maximum acceptance diameter, to thereby create a fluoroscopically-visible target for a conventional 0.014 inch guidewire. The interior of the funnel transitions continuously and smoothly into the through lumen 18 (FIG. 8) of inflatable funnel 16.

The funnel-like mouth 19 of inflatable funnel 16, and through-passing 0.014 inch inner lumen 18 of the inflatable funnel, are designed so that there is a smooth transition between the two, whereby to readily guide an advancing guidewire into the lumen of inflatable funnel 16 and then out to the sterile operative field (via second curved tube 11). See FIGS. 6-8, which provide further construction details of the inflatable funnel 16.

A crossing guidewire 17 (FIGS. 6-8) is also utilized in the "cross and receive" approach. Crossing guidewire 17 can preferably exhibit properties of a conventional coronary guidewire with several desirable characteristics, in particular, a 0.014 inch maximum diameter throughout, excellent distal radio-opacity to facilitate fluoroscopic visualization and/or distal ultrasonic visibility to facilitate echocardiographic visualization, and a flexible, atraumatic tip with adequate "crossability" to allow crossing guidewire 17 to be readily guided and tracked into the mouth of inflatable funnel 16. The proximal end of guidewire 17 may have features such as a reduced diameter (e.g., to allow it to readily dock with the spanning suture of the spanning implant in a manner which maintains a maximum crossing profile of 0.014 inch after docking).

The key steps of the "cross and receive" approach, using the apparatus just described, will now be presented.

First, first positioning sheath 5 of TCT3 is advanced through apical access sheath 1 and its distal end positioned adjacent to the posterior annulus (FIGS. 6 and 7). Then first curved tube 7 and guidewire 17 (which is preferably an RF puncture guidewire) are inserted into first positioning sheath 5 and positioned and affixed so that the tip of guidewire 17 emerges from the tip of the first curved tube 7 by approximately 1 mm or 2 mm, i.e., a distance sufficient to allow the RF action to "lead" the advancement of first curved tube 7 through the annulus on the posterior side of the mitral valve. RF guidewire 17 is connected to the RF generator and RF guidewire 17 and first curved tube 7 are passed through the posterior annulus. See FIGS. 6 and 7. First curved tube 7 is then withdrawn so that it is completely contained within first positioning sheath 5, with the distal ends of first curved tube 7 and first positioning sheath 5 nearly aligned. At this point, guidewire 17 will have been passed through the posterior annulus, with the distal end of guidewire 17 being disposed in the left atrium. Note that, optionally, steering tube 15 is disposed between the first positioning sheath 5 and first curved tube 7 (see FIGS. 6 and 7).

Next, second positioning sheath 5A of TCT4 is inserted through apical access sheath 1 and positioned against the anterior annulus in the desired anchor location, with the line of action of the distal curved section being oriented so as to point into the left atrium and towards the opposite planned annular anchor point. This is done under ultrasound and/or fluoroscopic guidance. The target anatomical locations will, in normal practice, be selected in advance based upon echocardiogram, computer tomography and fluoroscopic data.

Then, second curved tube 11 (FIGS. 6 and 7) and an RF puncture wire are inserted into second positioning sheath 5A and positioned and affixed so that the tip of the RF puncture wire emerges from the tip of second curved tube 11 by approximately 1 mm or 2 mm, i.e., a distance sufficient to allow the RF action to "lead" the advancement of second curved tube 11 through the annulus on the anterior side of the mitral valve. The RF generator is turned on, and second curved tube 11 and the RF puncture wire are simultaneously advanced, as an assembly, along a curved path through the anterior annulus as defined by the pre-curve of the devices. Advancement continues until second curved tube 11 and the RF puncture wire emerge into the left atrium sufficiently far that second curved tube 11 is generally parallel with respect to the mitral annulus plane, and oriented by rotation so as to point at the opposite planned anchor point.

Alternatively, a dedicated custom puncture wire with a matched curve could be employed in place of the RF puncture wire and advanced independently into the left atrium, and then second curved tube 11 tracked over the dedicated custom puncture wire. It is also possible to form second curved tube 11 with a sharp distal tip, in which case it may be pushed through the anterior annulus without the assistance of a puncture wire.

While stabilizing second curved tube 11 and the RF puncture wire, second positioning sheath 5A of TCT4 is then retracted, leaving second curved tube 11 and the RF puncture wire in position.

The RF puncture wire is then withdrawn, and inflatable funnel 16 is advanced through second curved tube 11 and into the left atrium. If desired, a 0.014 inch guidewire may first be tracked through second curved tube 11 and into the left atrium so as to assist advancement of inflatable funnel 16 and so as to maintain proper positioning of inflatable funnel 16 in the left atrium.

With inflatable funnel 16 positioned in the left atrium, the proximal end of inflatable funnel 16 is locked to second curved tube 11 for stability. Then the inflatable funnel 16 is inflated, preferably with contrast agent. See FIGS. 6-8.

Steering tube 15 of TCT3 is then adjusted under both echocariodogram and multi-view fluoroscopic guidance so that first curved tube 7 (and hence crossing guidewire 17) is pointed towards the center of inflatable funnel 16. See FIGS. 6-8.

Crossing guidewire 17 is then advanced into the lumen of inflatable funnel 16 and then into the lumen of second curved tube 11. Crossing guidewire 17 is advanced until it exits from the proximal end of apical access sheath 1 in the operative sterile field. This completes positioning of the crossing guidewire via the "cross and receive" approach.

The three approaches discussed above (i.e., the "cross and snare" approach, the "cross and catch" approach and the "cross and receive" approach), provide highly accurate and controllable means for routing a crossing guidewire (and, subsequently, a spanning implant) along a structurally preferred path from the ventricular side of the mitral annulus, through the mitral annulus to the left atrium, across the mouth of the valve along a desired path, and then back through the annulus on the opposite side of the valve so as to extend into the left ventricle.

In this novel fashion, the method of the present invention allows for targeting a wide range of structural landmarks while avoiding the possibility of entanglement or interference with ventricular structures such as the chordae tendinea and papillary muscles. Furthermore, the procedure can be performed through a single, low-profile apical access sheath, using a limited set of operative procedures well within the skill of the average interventional clinician. Additionally, and as will hereinafter be discussed, successive, additional spanning passes can be made to effect progressive change to the valve shape in response to observed shape and functional regurgitation on real-time continuous echocardiography.

Other features may be added to the aforementioned apparatus to effect more preferred embodiments. One such feature may be the addition of a compliant balloon on the outer distal tip of the positioning sheath (e.g., first positioning sheath 5, second positioning sheath 5A, etc.). This compliant balloon would normally be inflated once the distal end of a positioning sheath is nearly in place against the target location on the ventricular side of the annulus. This compliant balloon would serve at least two purposes. First, when filled with a contrast agent, the compliant balloon would provide both an echocardiogram- and fluoroscopically-visible target on the tip of positioning sheath so as to improve clinical confidence when navigating the positioning sheath against the mitral annulus. Second, the compliant balloon tip would provide a more stable and atraumatic contact of the positioning sheath against the ventricular side of the annulus. An additional possible refinement of a positioning sheath is the addition, by various means, of either echo-attenuating or echo-genic structures and surfaces to the tip of a positioning sheath. A positioning sheath might, in an unmodified state, be fabricated from a material such as stainless steel or Nitinol tubing that would, in the as-manufactured state, create strong, directional echo reflections. The addition of diffusing and attenuating coatings on the distal end of a positioning sheath could render the positioning sheath more readily visible by echocardiographic means. In addition, by attenuating highly directional reflections along the shaft of a positioning sheath, the additional option exists to add echogenic features (such as grooves) or discrete echogenic structures (such as air-entrapping coils), such that specific points on the positioning sheath, preferably the distal tip, are rendered more echogenic.

5. Positioning of the Spanning Implant Across the Mitral Annulus

Once the crossing guidewire is in place, preferably using one of the procedures discussed above (e.g., the "cross and snare" approach, the "cross and catch" approach and the "cross and receive" approach), it is a relatively straightforward matter to effect the implantation and controlled adjustment of the spanning implant. These devices and steps will be described below and can be further appreciated by reference to the figures.

Implantation of the spanning implant can be conducted proceeding from either the anterior side or the posterior side of the crossing guidewire. The crossing guidewire may be constructed of conventional metallic guidewire elements, including combinations of coil, tube and solid elements, to vary the properties of the crossing guidewire from distal end to proximal end. Furthermore, a preferred embodiment of the crossing guidewire includes a pre-prepared continuous transition to the spanning suture of the spanning implant so that, when the spanning implant is to be positioned across the mitral valve, there is already a continuous length of spanning suture routed through the annulus, extending from the operative sterile field, through one side of the annulus from left ventricle to left atrium, across the left atrium, back down through the annulus from left atrium to left ventricle, and then back out into the operative sterile field.

The spanning implant preferably comprises conventional cardiovascular suture, in combination with pre-mounted and procedure-mounted anchoring and covering elements, as discussed below. More particularly, and looking now at FIG. 15, in one form of the present invention, a spanning implant 100 comprises a spanning suture 105 having a first end 110, a second end 115 and a first anchor 120 secured to first end 110 of spanning suture 105. The spanning implant also comprises a second anchor 125 which is fit over second end 115 of spanning suture 105, slid along spanning suture 105 to an appropriate position and then secured in place, preferably using a coaxial suture lock 130, as will hereinafter be discussed.

The spanning suture of the spanning implant is, in one preferred embodiment, a section of suitable permanent, non-bioabsorbable, hemocompatible suture, preferably either PTFE- or ePTFE-covered braided polyester suture. The size of the spanning suture is preferably in the range of 2-0 or larger, given the tensile load expected in this particular application, while presenting a PTFE surface to the blood so as to provide for hemocompatible surface properties. Preferably the spanning suture has a starting length of 25-40 cm to facilitate handling, routing and tensioning. However, only a much smaller portion of this length will ultimately become part of the spanning implant, as discussed below.

Figure 12:
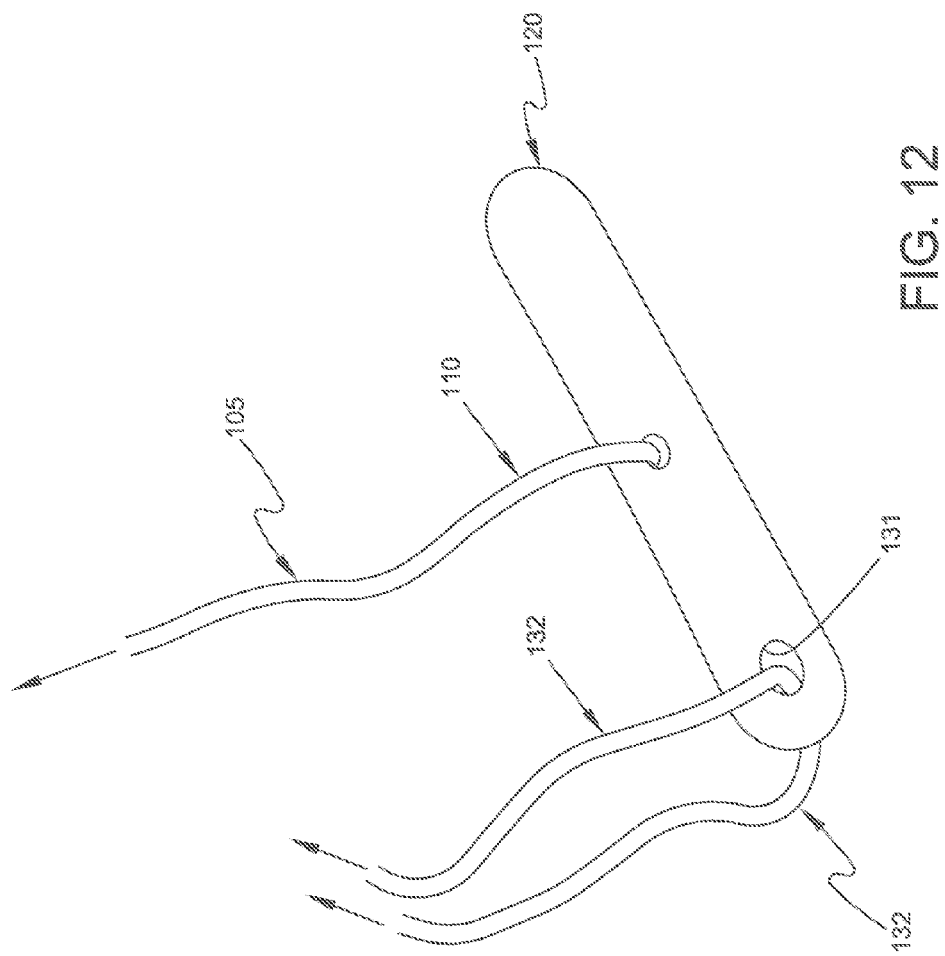
FIG. 12 is a schematic view showing a typical T-bar anchor which may be used to form the aforementioned first, fixed anchor set at the first end of the spanning suture, and also a control line for controlling the disposition of the T-bar anchor.

In one preferred form of the invention, one end of spanning suture 105 is pre-fitted with a T-bar anchor (i.e., the aforementioned first, fixed anchor 120), preferably made out of 316 stainless steel, titanium, PTFE or other material well known for durable permanent implantation, and also preferable fitted with one or several radiopaque markers, typically tantalum, and optionally coated and buffered with pledgets or a polyester cover. One preferred configuration of first, fixed anchor 120 is shown in FIG. 12. In one preferred embodiment, the T-anchor 120 is provided with a through-hole 131 to allow a control line 132 to be passed through the anchor on one end, or possibly on both ends of the anchor. As will be described further below, such a control line 132 will, in conjunction with spanning suture 105, allow the T-anchor 120 to be re-positioned once the T-anchor is in place, particularly if a stiffening sleeve is fitted over control line 132 to provide for both tension and lateral steering of T-anchor 120.

Figure 15:
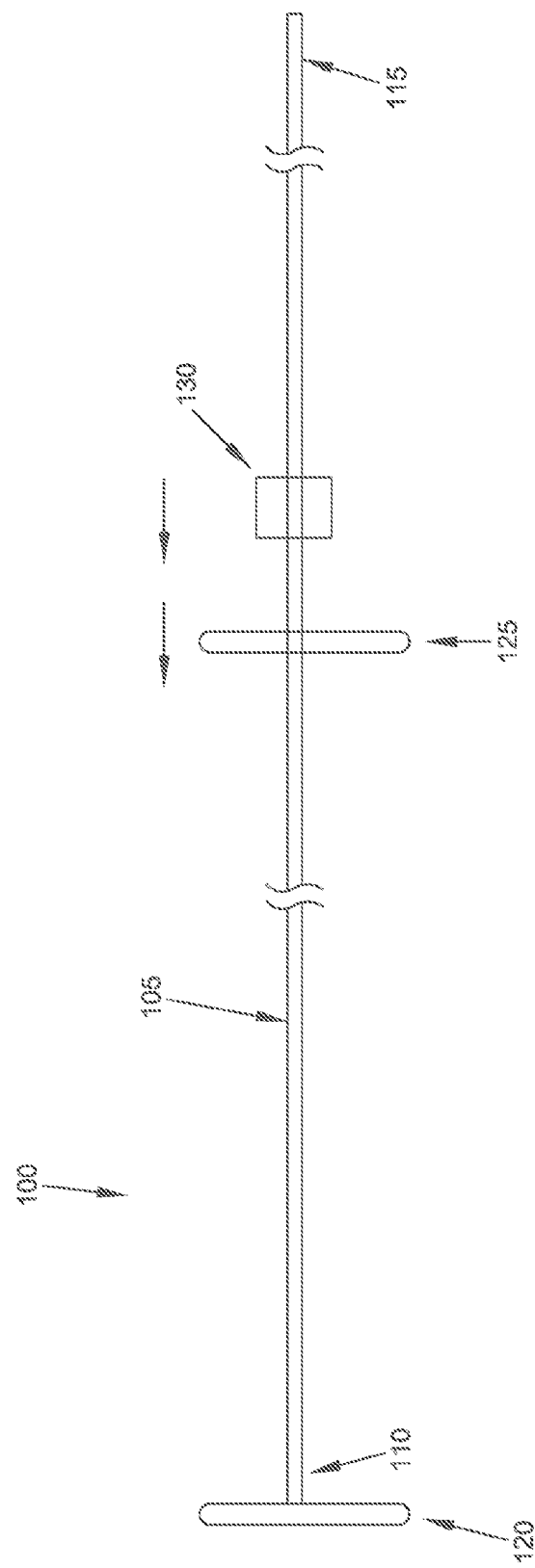
FIG. 15 is a schematic view showing one preferred form of a spanning implant formed in accordance with the present invention.

In one preferred embodiment, the opposing end of spanning suture 105 (i.e., second end 115, as seen in FIG. 15) is further fitted with a "docking" feature so that the spanning suture can be attached to the crossing guidewire in a conventional, coaxial manner. Such docking feature may be effected by various constructions. By way of example but not limitation, a simple approach is to tie a knot of suitable configuration between the spanning suture, factory-terminated, onto the back of the crossing guidewire as previously described. Alternatively, the docking feature may be provided with a coaxial screw lock feature as is conventionally found on docking guidewires employed to facilitate "over the wire" catheter exchanges. In another approach, the ends of the spanning suture may be temporarily fused, using thermal or adhesive means, so as to form an attachment with the crossing guidewire. Or the ends of the spanning suture may be connected with a tubular mechanical crimped, fused or bonded lock, whereby to secure the spanning suture to the crossing guidewire.

Prior to routing spanning suture 105 across the annulus, it is further anticipated that, in one preferred embodiment, a tubular "tissue grommet" or dedicated pledget 135 (FIG. 16) will be employed to further enhance the characteristics of the spanning implant. More particularly, the tissue grommet may consist of a PTFE sleeve, with an approximately 0.042 inch outer diameter, an approximately 0.014 inch inner diameter, and a flange on one end. Alternatively, the tissue grommet may have an additional cover of, or be completely formed out of, Dacron or ePTFE. In the preferred embodiment, it is expected that equivalent tissue grommets will be placed in the posterior and anterior annulus (see FIG. 16). The primary purpose of the tissue grommet is to protect the annular tissue as the spanning suture is routed into position. An additional role of the tissue grommet is to enhance the durability of the spanning implant by enabling tissue in-growth into the surface of the grommet, thus providing for a more robust passage of the spanning suture through the annulus. See FIG. 16, which shows grommets 135 protecting the annular tissue where spanning suture 105 passes through the annulus.

The tissue grommet is also supplied with an advancing sheath to allow the tissue grommet to be advanced, in a conventional fashion, over the crossing guidewire and placed into the annulus.

An implant-advancing sheath is preferably provided to allow for ready advancement of first, fixed anchor 120 into position under the annulus.

Figure 13:
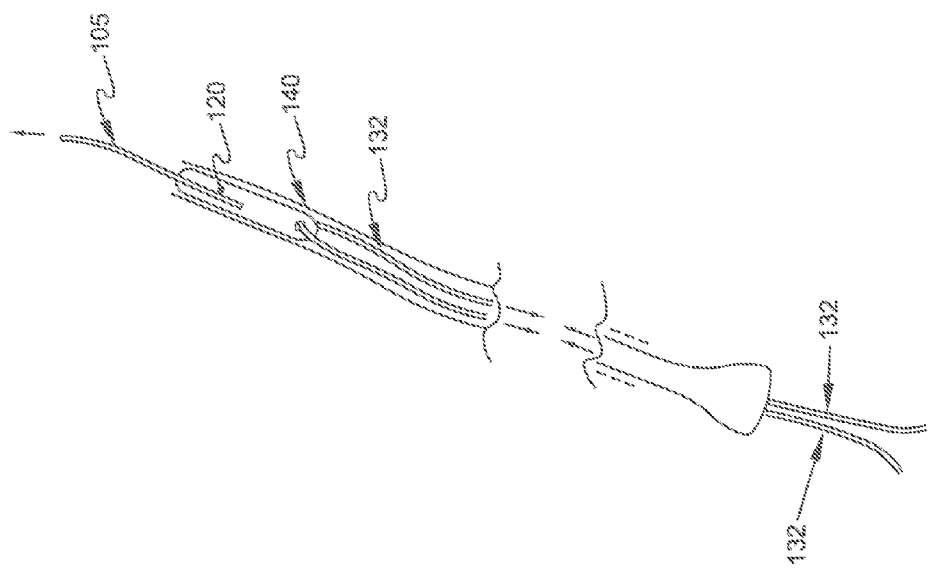
FIG. 13 is a schematic view showing a sheath which may be used to deploy the first, fixed anchor and the spanning suture.

The implant advancing sheath 140 (FIG. 13) preferably comprises an approximately 6 French to approximately 9 French tubular construction with a central through lumen suitable to accommodate the T-bar anchor 120. In a preferred embodiment, the distal end of implant advancing sheath 140 may be shaped to accommodate the T-anchor 120.

Positioning of the spanning implant across the mitral annulus will now be described. For purposes of example but not limitation, the implantation sequence will be described beginning from the anterior (trigone) side of the annulus, although it could also be conducted beginning from the posterior side of the annulus.

With the spanning guidewire in place, a tissue grommet 135 is advanced over the guidewire and into position through the posterior annulus. The grommet advancing tool is then removed. The proximal end (anterior side) of the crossing guidewire is then, as described above, terminated (by one of several means) to the distal end of the spanning suture, and with the spanning implant further loaded into the implant advancing catheter 140. In a preferred embodiment, the T-bar anchor 120 and implant advancing catheter 140 are provided, already-assembled, for use in the clinical setting.

The spanning implant is then advanced through the annulus by withdrawing the crossing guidewire from the distal end of the guidewire until the first, fixed anchor 120 reaches the ventricular side of the anterior annulus. The spanning suture is held in place while the implant advancing sheath 140 is withdrawn sufficiently far to allow the T-bar anchor 120 to tip over into place.

The implant advancing sheath 140 is then removed. At this time, if provided, control line 132 is employed to adjust the orientation of T-bar anchor 120. As required, the control line is fitted with a stabilizing sleeve. At any chosen point in the procedure, the control line can be readily removed from the T-bar anchor 120 by sliding the control line 132 out of the body of the T-bar anchor 120. In the preferred embodiment shown in FIGS. 12 and 13, the control line 132 can be immediately removed by withdrawing the control line, e.g., by pulling out either free end of the control line.

A posterior grommet 135 is advanced over second end 115 of spanning suture 105 until it is seated in the posterior annulus in a fashion identical to the anterior side grommet. The grommet advancing tool is then removed.

At this point, the spanning implant has its fixed T-bar anchor 120 positioned against the ventricular side of the anterior annulus and the spanning suture extending through the anterior annulus, across the left atrium, through the posterior annulus and back out the left ventricle, with grommets positioned over the spanning suture as the spanning suture extends through the anterior annulus and the posterior annulus.

6. Implant Sizing and Termination

The final step in the procedure is sizing and termination of the spanning implant, comprising the tools and steps described below.

A second, sliding anchor 125 (FIG. 15) and coaxial suture lock 130 (FIG. 15) are provided. Second, sliding anchor 125 preferably comprises a T-bar anchor, preferably 316 stainless steel, titanium, PTFE or other material or combination of materials known for durable permanent implantation, and also preferably fitted with one or several radiopaque markers, typically tantalum, and finally coated and buffered with pledgets or a polyester cover. This T-bar anchor 125 can be advanced coaxially over the second end 115 of spanning suture 105 so as to be brought up against the ventricular side of the posterior annulus and fixed in place (FIG. 16), as will hereinafter be discussed.

Figure 14:
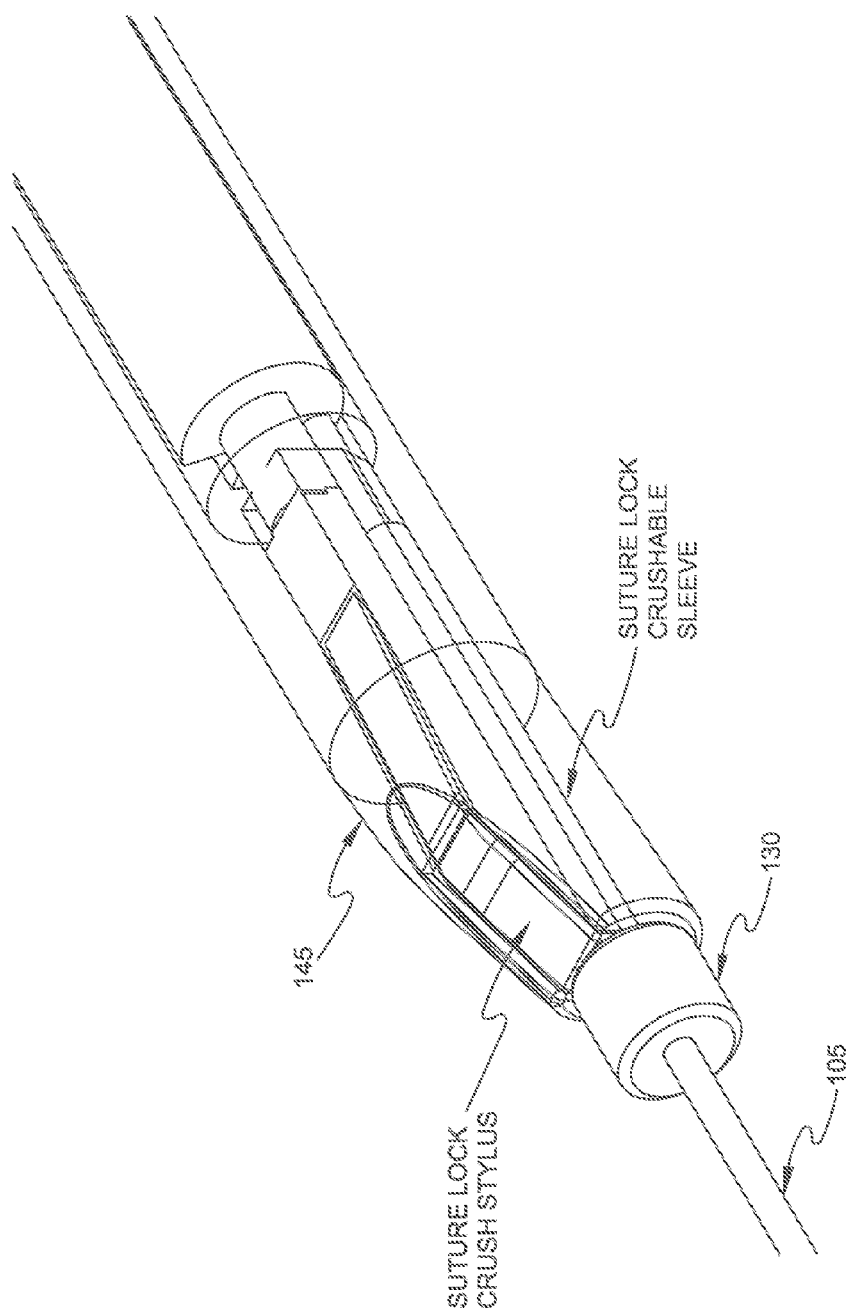
FIG. 14 is a schematic view showing the distal end of a preferred form of implant tensioning tool, sometimes hereinafter referred to herein as a "Span-Tension-Terminate Tool" (STTT), including spanning suture and coaxial suture lock.

As an alternative to T-bar anchors, a screw-in anchor, providing for central routing of the spanning suture, could be employed as a general substitute for the sliding T-bar anchor 125. By way of example but not limitation, in one preferred embodiment, a suture-locking anchor (preferably formed out of stainless steel or titanium) comprises a proximal component and a distal component which are threaded together so as to effect locking onto the spanning suture, possess a central hole for passing the spanning suture, and have tines or other features to permanently lock onto the spanning suture when the threads are fully engaged. An alternative preferred embodiment for the second, sliding anchor 125 is a construction comprising a metallic sleeve and various other mating features to the T-bar anchor 125. In this embodiment, locking would be achieved by plastically deforming the sleeve section so as to effect permanent attachment to the spanning suture. In one preferred form of the invention, the second, sliding anchor 125 and coaxial suture lock 130 are loaded within, and applied to, the spanning suture by the aforementioned implant tensioning tool, such as a "Span-Tension-Terminate Tool" (STTT) 145 (FIG. 14). More particularly, and looking now at FIG. 14, the spanning suture is routed coaxially through the STTT and the coaxial suture lock 130. The coaxial suture lock is fitted to the distal end of the STTT and maintained in position by lightly drawing on the crush stylus so as to hold the coaxial suture lock 130 in position in the distal end of the STTT.

The STTT allows the clinician to controllably tension and then terminally anchor the spanning suture, with the spanning suture being held under tension between the T-bar anchor 120 set on the anterior side of the annulus and the locking anchor 125 set on the posterior side of the annulus (see FIG. 16). There are various other means of achieving the same suture locking action well known in the mechanical arts, including the use of a collet-and-sleeve action or a tapered wedge action or a wedging pin forced into a constraining sleeve, etc.

STTT is contained within an overall 7-9 French reinforced sheath to facilitate control and delivery of the spanning implant.

In the operative field, the second end 115 of the spanning suture is routed through the second, sliding anchor 125 and the STTT.

The STTT is advanced over the spanning suture until the second, sliding anchor 125 and the coaxial suture lock 130 reach the posterior annulus. Alternatively, the second, sliding anchor 125 may be delivered independently of the STTT using the technique already described. If such an approach is employed, the second, sliding anchor 125 is fitted with a stabilizing grommet so that when it is deployed on the ventricular side of the annulus, the second, sliding anchor 125 remains in position while the anchor delivery sleeve is removed and the STTT routed into position.

In the case where the second, sliding anchor 125 is fitted integrally to the STTT, the second, sliding anchor 125 is first moved from the insertion position to the seated position in the same fashion as described above. A sliding outer sleeve fitted on the STTT may be employed to achieve similar effect.

The spanning suture is then tensioned through the STTT to progressively decrease the anterior/posterior dimension, and hence progressively reduce the mitral regurgitation of the valve. This adjustment is done in increments with observation periods in between while under real-time echo, fluoro, and EKG monitoring. If desired, the STTT can be provided with means for continuously measuring and displaying the tension applied to the spanning suture as the therapeutic input is applied. The STTT may also be provided with means for continuously measuring the length of the spanning suture withdrawn into the STTT. And the STTT may be provided with means for withdrawing the spanning suture in pre-defined increments such as 1 mm, e.g., by the provision of a ratchet and pawl mechanism. Or the STTT may be provided with a one-way clutch to maintain tension on the spanning suture through the STTT, e.g., by a one-way needle-bearing clutch of the sort well-known in the medical arts. Also, the STTT may include a motorized withdrawal of the spanning suture, e.g. with a small gear motor and the provision of calibrated retraction steps, again, such as 1 mm per increment.

When the desired anterior/posterior ("A/P") dimension of the mitral valve has been achieved, and hence the desired reduction of mitral regurgitation has been effected, the coaxial suture lock 130 is deployed by the STTT by rotating a handle on the proximal end of the STTT which causes one component of the coaxial suture lock to rotate while the other component is held in place by the STTT. Thus, the suture lock is threaded together, the second, sliding anchor 125 is engaged, and the spanning suture is locked in place under the appropriate tension. Alternatively, the STTT can operate so as to permanently deform a crushable anchor via the translation or other actuation of a locking mechanism that serves to deform the suture lock, thus affixing a permanent diametrical lock onto the spanning suture in such a manner that the final treatment tension of the spanning suture is precisely secured.

The STTT is then removed coaxially over the suture.

Alternatively, the STTT could be provided in a so-called "rapid exchange" configuration, i.e., the spanning suture is exited from the shaft of the STTT at a point relatively distal on the STTT, which thus allows more independent handling of the spanning suture or guidewire in the operative sterile field. The STTT would otherwise function as when provided in a conventional coaxial or "over-the-wire" form.

The distal end of the spanning suture may then be cut proximal to the now-fixed second anchor 125. Alternatively, it may be terminated to a pledget outside the left ventricle wall, to leave a tether to the implant assembly, thereby guaranteeing that even if the spanning implant becomes loose, it will not embolize and travel in the bloodstream through the body, potentially causing injury.

FIG. 16 shows a spanning implant 100 positioned across a mitral valve. As seen in FIG. 16, first, fixed anchor 120 is positioned against the ventricular side of the anterior annulus, spanning suture 105 extends through the anterior annulus, across the left atrium, and through the posterior annulus, where second anchor 125, secured by coaxial suture lock 130, bears against the ventricular side of the posterior annulus, whereby to hold the reconfigured mitral annulus under tension. As shown in FIG. 16, grommets 135 preferably line the portions of the anterior annulus and the posterior annulus where the spanning suture passes through the annulus. However, it should also be appreciated that the use of grommets 135 is purely optional to the procedure.

7. Additional Spanning Implants

Additional spanning implants may then be electively deployed across the mitral annulus as needed so as to provide correction in one or more other locations, to increase the A/P reduction as needed, and to distribute the A/P reduction forces among a greater number of spanning implants.

It should be appreciated that the sequence described above could, alternatively, be applied simultaneously to multiple spanning implants, in particular through the use of a "temporary" STTT on one spanning implant while a conventional, permanent-anchoring STTT is employed on a second spanning implant. Such an approach would provide the clinical advantage of allowing for more complete consideration of various geometric and structural changes to the valve. In a particular preferred embodiment of a multiple-spanning implant approach, one spanning implant would be placed from the posterior trigone to a position on the posterior annulus approximately at the intersection of the P2 and P3 cusps of the posterior leaflet. Similarly, a second spanning implant would be effected between the anterior trigone and a position on the posterior annulus approximately at the intersection of the P1 and P2 cusps. These two spanning implants would effect balanced control of the valve with respect to the central aortic-mitral structural axis.

To complete the procedure, the apical access sheath is removed and the apical and chest wall access closed and the patient recovered.

MODIFICATIONS

The foregoing is considered to be only illustrative of the principles of the present invention. Since numerous modifications and changes will readily occur to those skilled in the art, the present invention is not limited to the exact constructions and operation shown and described above. While the preferred embodiment has been described, the details may be changed without departing from the spirit and scope of the present invention.

What is claimed is:

1. A method for repairing a mitral valve, the method comprising:
   positioning a crossing guidewire across the mitral valve, the crossing guidewire passing through the apex of the heart and into the left ventricle, across the left ventricle, through the annulus of the mitral valve at a first location and into the left atrium, across the left atrium, through the annulus of the mitral valve at a second location and back into the left ventricle, across the left ventricle, and back through the apex of the heart to exit the heart;
   using the crossing guidewire to position a spanning implant that extends from the left ventricle, through the annulus of the mitral valve at the first location and into the left atrium, across the left atrium, and through the annulus of the mitral valve at the second location, and into the left ventricle;
   anchoring the spanning implant at the first location with a first anchor, the first anchor being positioned against the left ventricle side of the annulus at the first location;
   tensioning the spanning implant so as to draw the first location and the second location closer together; and
   anchoring the spanning implant at the second location with a second anchor, the second anchor being positioned against the left ventricle side of the annulus at the second location.

2. A method according to claim 1 wherein the crossing guidewire is positioned across the mitral valve by:
   passing a first guidewire through the apex of the heart and into the left ventricle, across the left ventricle, through the annulus of the mitral valve at the first location and into the left atrium; passing the first guidewire from the left atrium through the valve leaflets, back into the left ventricle, across the left ventricle, back through the apex of the heart to exit the heart and out to an operative sterile field;
   passing a second guidewire through the apex of the heart and into the left ventricle, across the left ventricle, through the annulus of the mitral valve at the second location and into the left atrium;
   passing the second guidewire from the left atrium through the valve leaflets, back into the left ventricle, across the left ventricle, back through the apex of the heart to exit the heart and out to the operative sterile field;
   terminating an end of the first guidewire to an end of the second guidewire at the operative sterile field so as to create the complete crossing guidewire; and
   passing the termination from the operative sterile field through the apex of the heart and into the left ventricle, across the left ventricle, and through the valve leaflets, to the left atrium.

3. A method according to claim 2 wherein the first guidewire is passed across the left ventricle, through the annulus of the mitral valve and into the left atrium at the first location by advancing a first positioning sheath across the left ventricle so that the distal end of the first positioning sheath is positioned against the left ventricle side of the annulus at the first location, advancing a first curved tube out of the first positioning sheath and through the annulus at the first location, and advancing the first guidewire through the first curved tube and into the left atrium.

4. A method according to claim 3 wherein the first curved tube has a sharp distal end so that it may be pushed through the annulus.

5. A method according to claim 3 wherein the first curved tube receives an RF wire therein, and further wherein the RF wire is used to create an opening in the annulus for receiving the first curved tube.

6. A method according to claim 2 wherein the first guidewire is passed from the left atrium, through the valve leaflets, back into the left ventricle, across the left ventricle, back through the apex of the heart to exit the heart and out to operative sterile field by advancing a snare from the left ventricle, through the valve leaflets and into the left atrium, snaring the first guidewire with the snare, and retracting the snare from the left atrium, through the valve leaflets and across the left ventricle.

7. A method according to claim 2 wherein the second guidewire is passed across the left ventricle, through the annulus of the mitral valve and into the left atrium at the second location by advancing a second positioning sheath across the left ventricle so that the distal end of the second positioning sheath is positioned against the left ventricle side of the annulus at the second location, advancing a second curved tube out of the second positioning sheath and through the annulus at the second location, and advancing the second guidewire through the second curved tube and into the left atrium.

8. A method according to claim 7 wherein the second curved tube has a sharp distal end so that it may be pushed through the annulus.

9. A method according to claim 7 wherein the second curved tube receives an RF wire therein, and further wherein the RF wire is used to create an opening in the annulus for receiving the second curved tube.

10. A method according to claim 2 wherein the second guidewire is passed from the left atrium through the valve leaflets, back into the left ventricle, across the left ventricle, back through the apex of the heart to exit the heart and out to operative sterile field by advancing a snare from the left ventricle, through the valve leaflets and into the left atrium, snaring the second guidewire with the snare, and retracting the snare from the left atrium, through the valve leaflets and across the left ventricle.

11. A method according to claim 1 wherein the crossing guidewire is positioned across the mitral valve by passing the crossing guidewire through the apex of the heart and into the left ventricle, across the left ventricle, through the annulus of the mitral valve at the first location and into the left atrium; passing a funnel-shaped snare through the apex of the heart and into the left ventricle, across the left ventricle, through the annulus of the mitral valve at the second location and into the left atrium; capturing the crossing guidewire with the funnel-shaped snare in the left atrium; and retracting the funnel-shaped snare and captured crossing guidewire through the annulus at the second location and into the left ventricle.

12. A method according to claim 1 wherein the crossing guidewire is positioned across the mitral valve by passing the crossing guidewire through the apex of the heart and into the left ventricle, across the left ventricle, through the annulus of the mitral valve at the first location and into the left atrium; passing an inflatable funnel through the apex of the heart and into the left ventricle, across the left ventricle, through the annulus of the mitral valve at the second location and into the left atrium while the inflatable funnel is in a deflated condition;

inflating the inflatable funnel; and advancing the crossing guidewire into the inflatable funnel and through the annulus at the second location, and into the left ventricle.

13. A method according to claim 1 wherein the spanning implant is positioned so that it extends from the left ventricle, through the annulus of the mitral valve at the first location, across the left atrium, through the annulus of the mitral valve at the second location, and into the left ventricle by attaching the spanning implant to the crossing guidewire and using the crossing guidewire to pull the spanning implant into position.

14. A method according to claim 1 wherein the spanning implant comprises a suture having a first end and a second end, the first anchor being secured to the first end of the suture, the second anchor slidably mounted to the second end of the suture, and the spanning implant further comprising a coaxial suture lock for locking the second anchor to the suture.

15. A method according to claim 1 wherein the spanning implant is dynamically tensioned while observing changes in the function of the mitral valve.

16. A method according to claim 14 wherein the first anchor comprises a T-bar anchor.

17. A method according to claim 16 further comprising a control line releasably secured to the T-bar anchor.

18. A method according to claim 14 wherein the second anchor comprise a T-bar anchor.

19. A method according to claim 14 wherein the coaxial suture lock is configured to bind to the suture upon the application of a compressive radial force to the coaxial suture lock.

\* \* \* \* \*